US010441315B2

United States Patent
Suh et al.

(10) Patent No.: US 10,441,315 B2
(45) Date of Patent: Oct. 15, 2019

(54) APPARATUS FOR LOADING FOLLICULAR UNIT INTO NEEDLE FOR HAIR IMPLANT

(71) Applicants: Electronics and Telecommunications Research Institute, Daejeon (KR); Kyungpook National University Industry-Academic Cooperation Foundation, Daegu (KR)

(72) Inventors: Jung Wook Suh, Daegu (KR); Moon Kyu Kim, Daegu (KR); Jung Chul Kim, Daegu (KR); Yong Chul Jung, Daegu (KR); Eun Chang Choi, Daegu (KR)

(73) Assignees: Electronics and Telecommunications Research Institute, Daejeon (KR); Kyungpook National University Industry-Academic Cooperation Foundation, Daegu (KR)

( * ) Notice: Subject to any disclaimer, the term of this patent is extended or adjusted under 35 U.S.C. 154(b) by 330 days.

(21) Appl. No.: 15/230,515

(22) Filed: Aug. 8, 2016

(65) Prior Publication Data

US 2017/0135713 A1    May 18, 2017

(30) Foreign Application Priority Data

Nov. 12, 2015  (KR) .................... 10-2015-0158819

(51) Int. Cl.
*A61B 17/34* (2006.01)
*A61B 17/00* (2006.01)
(Continued)

(52) U.S. Cl.
CPC .... *A61B 17/3468* (2013.01); *A61B 17/22031* (2013.01); *A61B 2017/0053* (2013.01);
(Continued)

(58) Field of Classification Search
CPC ... A61B 17/221; A61B 17/30; A61B 17/3468; A61B 2017/00544; A61B 2017/00752;
(Continued)

(56) References Cited

U.S. PATENT DOCUMENTS 4,611,594 A * 9/1986 Grayhack ............ A61B 17/221
                                                 606/127
5,417,683 A * 5/1995 Shiao ................. A61B 17/3468
                                                 604/173

(Continued)

FOREIGN PATENT DOCUMENTS

| KR | 10-1155219 B1 | 6/2012 |
| KR | 10-1155258 B1 | 6/2012 |
| WO | WO 2007-041267 A2 | 4/2007 |

*Primary Examiner* — Jacob J Cigna
(74) *Attorney, Agent, or Firm* — Rabin & Berdo, P.C.

(57) ABSTRACT

Provided is an apparatus for loading a follicular unit to a needle for hair implant including a first slitless needle in which the other end of a hollow body has a wedge shape, one end of the hollow body has a tubular shape to facilitate force transmission, and an end surface of the one end is blunt, so as to be used in a transplantation region in hair transplant procedure, and a first instrument configured to push the follicular unit to an interior of the first needle to load the follicular unit to the interior of the first needle.

19 Claims, 18 Drawing Sheets

(51) Int. Cl.
 *A61B 17/30* (2006.01)
 *A61B 17/22* (2006.01)
 *A61B 17/221* (2006.01)

(52) U.S. Cl.
 CPC ............ *A61B 2017/00544* (2013.01); *A61B 2017/00752* (2013.01); *A61B 2017/2215* (2013.01); *A61B 2017/305* (2013.01)

(58) Field of Classification Search
 CPC .... A61B 2017/2215; A61B 2017/2217; A61B 2017/301; A61B 2017/303; A61B 2017/305; A61B 90/50
 See application file for complete search history.

(56) References Cited

U.S. PATENT DOCUMENTS

| | | | | |
|---|---|---|---|---|
| 5,538,008 | A * | 7/1996 | Crowe | A61B 10/06 600/564 |
| 5,782,843 | A | 7/1998 | Aasberg | |
| 5,817,120 | A * | 10/1998 | Rassman | A61B 17/3468 606/187 |
| 5,827,297 | A * | 10/1998 | Boudjema | A61B 10/0283 606/133 |
| 5,827,305 | A * | 10/1998 | Gordon | A61B 10/0266 606/159 |
| 5,944,728 | A * | 8/1999 | Bates | A61B 17/221 604/264 |
| 6,461,369 | B1 * | 10/2002 | Kim | A61B 17/3468 606/187 |
| 6,585,746 | B2 | 7/2003 | Gildenberg | |
| 7,144,406 | B2 * | 12/2006 | Pak | A61B 17/3468 606/187 |
| 8,211,134 | B2 | 7/2012 | Oostman, Jr. | |
| 8,882,783 | B2 | 11/2014 | Oostman | |
| 8,951,267 | B2 | 2/2015 | Oostman, Jr. | |
| 9,149,609 | B2 * | 10/2015 | Ansel | A61B 17/22031 |
| 2004/0092924 | A1 * | 5/2004 | Vasa | A61B 17/3468 606/32 |
| 2004/0193203 | A1 * | 9/2004 | Pak | A61B 17/3468 606/187 |
| 2006/0178678 | A1 * | 8/2006 | Cole | A61B 17/32053 606/133 |
| 2007/0078466 | A1 * | 4/2007 | Bodduluri | A61B 17/32053 606/133 |
| 2008/0009896 | A1 * | 1/2008 | Shiao | A61B 17/3468 606/187 |
| 2008/0051816 | A1 * | 2/2008 | Pak | A61B 17/3468 606/187 |
| 2009/0240261 | A1 * | 9/2009 | Drews | A61B 10/0266 606/133 |
| 2012/0041451 | A1 * | 2/2012 | Bodduluri | A61B 17/32053 606/133 |
| 2015/0133962 | A1 | 5/2015 | Oostman, Jr. | |
| 2016/0015424 | A1 * | 1/2016 | Kim | A61B 17/3468 606/187 |
| 2016/0045223 | A1 * | 2/2016 | Kim | A61B 17/3468 606/187 |
| 2018/0193058 | A1 * | 7/2018 | Bae | A61B 17/3468 |

* cited by examiner

APPARATUS FOR LOADING FOLLICULAR UNIT INTO NEEDLE FOR HAIR IMPLANT

CROSS-REFERENCE TO RELATED APPLICATIONS

This application claims priority under 35 U.S.C. § 119 to Korean Patent Application No. 10-2015-0158819, filed on Nov. 12, 2015, the disclosure of which is incorporated herein by reference in its entirety.

TECHNICAL FIELD

The present invention relates to an apparatus for loading a follicular unit into a needle for hair implant and, more particularly, to an apparatus for loading a follicular unit into a first hollow slitless needle for hair implant and loading the follicular unit into a needle for hair implant that may be used for hair transplant procedure.

BACKGROUND

In general, a hair transplant procedure is mainly performed in a strip manner in Korea. The hair transplant procedure may include anesthetizing process, a strip cutting process, a suturing process, a follicular unit extracting process, and a hair transplanting process using hair transplant equipment.

The follicular unit extracting process includes strip extraction and follicular unit extraction (FUE).

The strip extraction is a cutting scheme. According to the strip extraction, an operator extracts a strip as a long scalp from the back of the head of a patient, and sews the strip-extracted back of the head. The operator or an assistant separates a follicular unit from the extracted strip by units.

FUE is a non-cutting scheme. According to FUE, an operator directly extracts a follicular unit from the skin using a thin punching machine.

The hair transplanting process may be divided into a hair transplanting method using a manual hair transplanter and a hair transplanting method using pincettes. A slit refers to an opening or aperture.

In particular, in a hair transplanting process, slit may refer to a narrow hole formed in a transplantation region in advance with an exclusive tool such as a needle and a chisel having a width ranging from 0.8 to 1.2 mm before inserting a follicular unit into the transplantation region, or an operation of forming such a narrow hole in advance.

According to a hair transplanting method using pincettes, an operator forms a slit in a transplantation region in advance and pushes a follicular unit into the slit using pincettes, while directly holding the follicular unit.

In the hair transplanting method using a manual hair transplanter, there is no need to form a slit. That is, an operator manually loads a follicular unit into a slit needle of a manual hair transplanter and subsequently directly pierces a transplantation region with the slit needle. As a result, the follicular unit is implanted in the transplantation region. Here, the slit, which is formed on a side of a sharp-pointed hollow needle, refers to a long opening formed in a length direction of the needle. The slit needle refers to a needle for hair implant with a slit.

When the follicular unit is implanted in a transplantation region, the follicular unit is not pressed by pincettes. For this reason, the hair transplanting method using a manual hair transplanter may be a more advanced method than a hair transplanting method using pincettes.

A needle of a related art manual hair transplanter has a slit formed on the side thereof in order to load a follicular unit.

In order to load a follicular unit to a needle for a manual hair transplanter, the related art needle requires a slit.

An operation using a hair transplanter or implanter employs a scheme of loading a collected or separated follicular unit into a needle for implanter one by one and individually implanting the follicular unit in a transplantation region.

On this account, several implanters are required for hair transplantation. Here, for an implanting operation each time, an implanter is required to be replaced, resulting in limitations in an operation rate.

Also, a general practitioner or a surgeon, a nurse, or an assistant performing the surgical procedure have excessive fatigue, and a long surgical procedure makes a patient undergoing the surgical procedure to feel greatly pressed.

If automated hair transplant equipment capable of sequentially changing several needles having follicular units loaded therein is used for hair transplantation, a time for surgical procedure may be shortened and fatigue may be reduced.

In order to shorten a time for a surgical procedure and reduce fatigue, several needles need to be held in a cartridge (for example, a storage device) for hair transplant equipment. Here, when a needle having the same slit as that of existing manual hair transplant equipment is used, a hair member of a follicular unit sticks out from the needle. As a result, hair members may be entangled with each other. Also, the follicular unit may be separated from the needle.

Therefore, a needle used for automated hair transplant equipment is not required to have a slit as possible.

However, a unit for easily and quickly loading or inserting a follicular unit into a slitless needle is yet to exist.

SUMMARY

Accordingly, the present invention provides an apparatus for loading a follicular unit to a needle for hair implant, capable of allowing a follicular unit to be accurately and quickly loaded to a first slitless needle for hair implant by a mechanical unit or device, thus shortening a time for a surgical procedure of hair implant performed by a user such as a surgeon, a nurse, or an assistant assisting a surgeon or a nurse, to reduce the burden of the user or a patient.

In one general aspect, an apparatus for loading a follicular unit to a needle for hair implant includes: a first slitless needle in which the other end of a hollow body has a wedge shape, one end of the hollow body has a tubular shape to facilitate force transmission, and an end surface of the one end is blunt, so as to be used for hair transplant procedure; and a first instrument configured to push the follicular unit to an interior of the first needle to load the follicular unit to the interior of the first needle.

The first instrument may include: a second needle in which the follicular unit to be transmitted toward the first needle is disposed and a slit in which one side is closed and the other side is opened is formed on an outer circumferential surface of an end portion facing the first needle; a positioning jig configured to have an insertion hole, into which the first needle and the second needle are inserted, extending in a length direction of the jig, and coupled between the first needle and the second needle to adjust a center of the second needle and a center of the first needle; and a push rod inserted into the interior of the second needle in order to push the follicular unit of the second needle toward an internal space of the first needle.

The positioning jig may include: a front portion of the insertion hole having an inner diameter into which one end of the first needle having the tubular shape is inserted; a rear portion of the insertion hole having an inner diameter into which the end portion of the second needle having the slit is inserted; and a middle portion of the insertion hole formed between the front portion and the rear portion, having an inner diameter smaller than the inner diameter of the front portion and the inner diameter of the rear portion, and having a stop protrusion having a size into which the push rod is inserted.

The position jig may have a wedge portion formed at the rear end of the middle portion to receive a sharp end portion of the second needle so as to be press-fit to a sharp end portion of the second needle in terms of shape.

The positioning jig may include: a front portion of the insertion hole having an inner diameter into which one end of the first needle having the tubular shape is inserted; and a rear portion of the insertion hole having an inner diameter into which a flat end portion of the second needle with a slit is inserted, wherein the front portion and the rear portion may be integrally connected to each other and the inner diameter of the front portion and the inner diameter of the rear portion are equal.

The positioning jig may include: a front portion in which the follicular unit to be transmitted toward the first needle is disposed within the jig, a jig slit in which one portion is closed and the other portion is opened is formed, and the one end of the first needle having the tubular shape is inserted thereinto; and a rear portion integrally formed at the rear of the jig and having a guide hole into which the push rod is directly inserted.

The follicular unit may include: a hair bulb member having a diameter of a size by which the hair bulb member is movable within the first needle; and a hair member extending from a rear end of the hair bulb member.

The push rod may further include: a groove configured to receive the hair member, wherein one end of the groove may be opened at an end of the push rod facing the follicular unit.

The push rod may include: a spring support formed in a portion spaced apart from the groove toward the opposite end of the follicular unit; and a spring coupled between the spring support and the end facing the follicular unit, wherein one end of the spring is in contact with a side surface of the spring support and the other end of the spring is in contact with an outer end surface of the second needle.

One end of the spring may be fixed by a first fixture of the spring support, and the other end of the spring may be fixed by a second fixture of an outer end surface of the second needle.

In another general aspect, an apparatus for loading a follicular unit to a needle for hair implant includes: a first slitless needle in which the other end of a hollow body has a wedge shape, one end of the hollow body has a tubular shape to facilitate force transmission, and an end surface of the one end is blunt, so as to be used for hair transplant procedure; and a second instrument configured to pull the follicular unit toward the first needle to load the follicular unit to an interior of the first needle.

The second instrument may include: tweezers configured to have legs formed as an end thereof is bifurcated in order to grip or release a hair member, as a unit for gripping the follicular unit including a hair bulb member having a diameter of a size movable within the first needle and a hair member extending from a rear end of the hair bulb member; and a tweezer rod configured to have a diameter inserted into the interior of the first needle and connected to the tweezers, wherein when the tweezer rod moves, outer surfaces of the tweezers may come into contact with a hole edge of the first needle and the tweezers may become closer to grip the hair member.

The second instrument may further include: a guide tube inserted into the tweezer rod and interposed between the tweezer rod and the first needle.

The second instrument may include: a stent having a mesh structure for gripping or releasing the hair member or the hair member, as a unit for gripping the follicular unit including a hair bulb member having a diameter of a size that can be movable within the first needle and a hair member extending from a rear end of the hair bulb member; and a stent rod having a diameter that can be inserted into the interior of the first needle and connected to the stent, wherein when the stent rod moves, an outer surface of the stent may come into contact with the hole edge of the first needle and, as the volume of the stent is reduced, the stent may grip the hair member.

In the second instrument, as the stent rod moves forwards or backwards in a length direction thereof within the first needle or as the stent rod is rotated in a circumferential direction thereof, the volume of the stent connected to the stent rod and having elastic force may expand or contract.

In another general aspect, an apparatus for loading a follicular unit to a needle for hair implant includes: a first device or a second device including: a first slitless needle in which the other end of a hollow body has a wedge shape, one end of the hollow body has a tubular shape to facilitate force transmission, and an end surface of the one end is blunt, so as to be used for hair transplant procedure; and an intake tube inserted into a needle interior of the first needle to pull the follicular unit toward the first needle and receiving intake pressure (here, the intake pressure refers to pressure lower than negative pressure formed by a pneumatic device or atmospheric pressure) from an external pneumatic device.

The first device may include: a holder configured to have a plurality of needle mounting recesses for disposing a plurality of first needles, to have a plurality of through holes provided on one side of the plurality of needle mounting recesses, and to have a plurality of follicular unit mounting recesses provided on the other side of the plurality of needle mounting recesses; and a gripper device configured to grip the plurality of first needles of the holder and transfer the plurality of first needles to an interior of a cartridge, wherein the intake tube or tweezers moves or move forwards to pass through each of the needle interiors of the plurality of first needles to approach the follicular unit disposed on each of the plurality of follicular unit mounting recesses, and the follicular unit may tightly attached to an end of the intake tube by intake pressure or gripped by the tweezers by the legs of the tweezers operated by contacting with each of the plurality of needles or an inner surface of a guide tube, and the intake tube or tweezers moves or move backwards and an end of the intake tube or the tweezers and the follicular unit are positioned within each of the plurality of first needles, and as the intake pressure is removed or as the tweezers or the guide tube moves backwards, the legs of the tweezers are released from each of the plurality of first needles or from an inner surface of the guide tube to remove grip power with respect to the follicular unit to thus allow the follicular unit to be loaded to the needle interior of each of the plurality of first needles.

The second device may include: a holder configured to have a plurality of needle mounting recesses for disposing a plurality of first needles, to have a plurality of through holes provided on one side of the plurality of needle mounting recesses, and to have a plurality of follicular unit mounting recesses provided on the other side of the plurality of needle mounting recesses; a cartridge disposed on one side of the holder; and a sweeper disposed on the other side of the holder and configured to sweep the plurality of first needles positioned on the plurality of needle mounting recesses into an interior of the cartridge.

The apparatus may further include: a third device configured to pull the follicular unit toward each of the plurality of first needles to insert the follicular unit into each of the plurality of first needles, instead of the first device or the second device, wherein the third device may include: a base plate; a holder installed on the base plate and configured to have a plurality of needle mounting recesses provided to allow the plurality of needles to be disposed thereon and have a plurality of insertion holes to be aligned with centers of the plurality of needle mounting recesses on one side of the plurality of needle mounting recesses; a cartridge mounting/dismounting block installed on the base plate, tightly attached to an outer surface of the holder in a length direction, and allowing a cartridge to be inserted therein; a sweeper slidably coupled to holder and configured to sweep the plurality of first needles respectively positioned on the plurality of needle mounting recesses toward the interior of the cartridge; a positioning jig installed on the base plate, tightly attached to a rear surface of the holder, and configured to have a plurality of guide grooves provided in a direction in which an insertion hole of the holder extends; a guide rail installed on the base plate and configured to extend backwards of the positioning jig; a moving block coupled to the guide rail to move along the guide rail; a first moving frame rotatably coupled to a hinge recess of the moving block and configured to move a second needle through an intake tube or a coupling hole of the holder; and a second moving frame configured to move a push rod positioned within the second needle on the basis of the first moving frame in order to push a follicular unit of the second needle to load the follicular unit to an interior of each of the plurality of needle.

In order to replace the moving block, a spring may be interposed between a rear surface of a front portion of the first moving frame and a front surface of the second moving frame in order to transmit power, and operations of the first moving frame and the second moving frame may be sequentially performed by an operation of a single actuator.

Other features and aspects will be apparent from the following detailed description, the drawings, and the claims.

DETAILED DESCRIPTION OF EMBODIMENTS

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art.

The terms used herein are for the purpose of describing particular embodiments only and are not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Hereinafter, embodiments of the present invention will be described in detail with reference to the accompanying drawings.

First Embodiment

Figure 1:
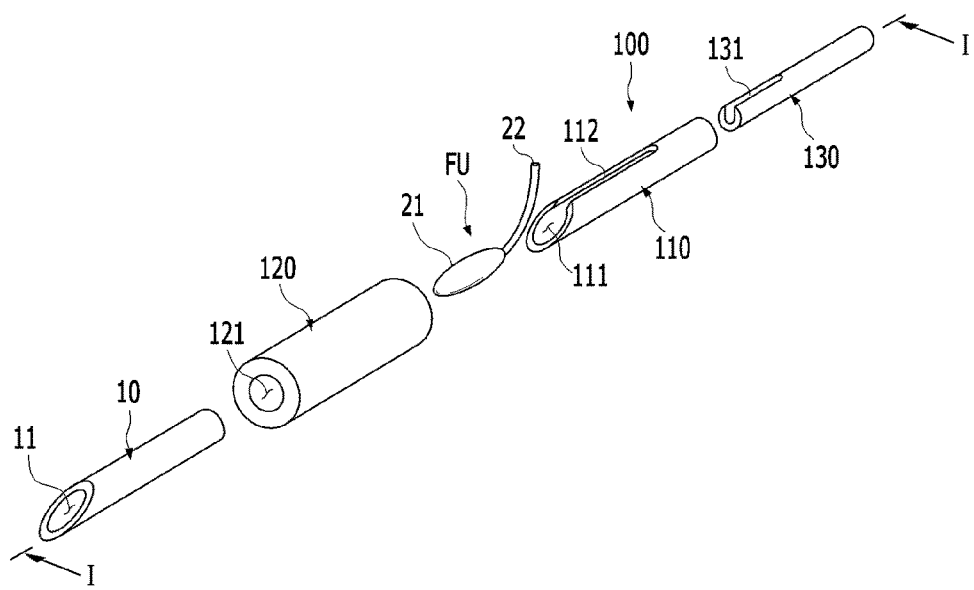
FIG. 1 is a perspective view illustrating a configuration of a first instrument of an apparatus for loading a follicular unit into a needle for hair implant according to a first embodiment of the present invention.
Figure 2:
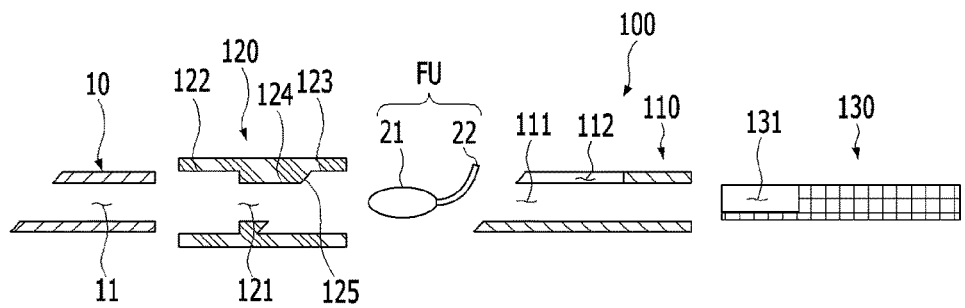
FIG. 2 is a cross-sectional view, taken along line I-I of FIG. 1.

FIG. 1 is a perspective view illustrating a configuration of a first instrument of an apparatus for loading a follicular unit into a needle for hair implant according to a first embodiment of the present invention, and FIG. 2 is a cross-sectional view, taken along line I-I of FIG. 1.

Referring to FIGS. 1 and 2, an apparatus for loading a follicular unit into a needle for hair implant includes a slitless first needle 10 and a first instrument 100.

The first needle 10 may be used to pierce into a transplantation region in a hair transplant procedure, or may be connected to a fixed needle for implant (not shown) of an implanter (not shown) to serve as a cylindrical cartridge storing a follicular unit.

For example, the first needle 10 is termed a needle for implanter actually used for hair implantation.

That is, the first needle 10 is a slitless needle for hair implant. Thus, when a plurality of first needles 10 are loaded in a single cartridge for hair implant or stacked in a cartridge in an automated implanter, hair member 22 of a follicular unit (FU) may not be entangled with a hair member of another follicular unit adjacent thereto.

In addition, the first needle 10 may be deformed to have a tube shape in which both ends are not sharp, rather than a shape in which only one end is sharp, to be manufactured. That is, the first needle 10 according to the modified example may be manufactured to have a tube type or cylindrical hollow cartridge form for simply storing the follicular unit. In this case, the follicular unit stored in the cylindrical cartridge may be connected to a fixed needle for implanter of an implanter and required to be additionally loaded for an implanting operation.

The follicular unit may include a hair bulb member 21 having a diameter with which the follicular unit is movable within the first needle 10 and a hair member 22 extending from a rear end of the hair bulb member 21.

The first needle 10 may have a hollow body having a tube shape, one end of the hollow body formed as a blunt end and the other end of the hollow body formed to have a wedge shape.

The first instrument 100 serves to push the follicular unit into an interior of the first needle 10 such that the follicular unit may be loaded into the interior of the first needle 10.

The first instrument 10 may be a sort of follicular unit loading device.

When the follicular unit and the first needle 10 are excluded, the first instrument 100 may basically have three components including a second needle 110, a positioning jig 120, and a push rod 130. When the first instrument 100 has the first needle 10 as an essential component, the first instrument 100 includes a total of four components, excluding the follicular unit.

The second needle 110 has a slit 112. The hair bulb member 21 of the follicular unit is positioned within a needle interior 111 of the second needle 110, the hair member 22 of the follicular unit may be positioned in the slit 112.

The second needle 110 serves to transmit the follicular unit to load or insert the follicular unit into the first needle 10.

In order for the follicular unit to be transmitted to the first needle 10, the follicular unit is disposed in the needle interior 111 of the second needle 110. The slit 112 is formed on an outer circumferential surface of an end portion orienting toward the first needle 10. One side of the slit 112 is closed, and the other side of the slit 112 is opened.

The positioning jig 120 serves to align the centers the second needle 110 and the first needle 10.

The positioning jig 120 may have an insertion hole 121 so as to be coupled between the first needle 10 and the second needle 110.

The insertion hole 121 extends in a jig length direction so as to be inserted into the first needle 10 and the second needle 110.

The insertion hole 121 may have a structure punctured to have a straight form in a length direction, or may have a step or an installation recess formed therein to easily adjust the center of the first needle 10 and the center of the second needle 110.

The positioning jig 120 includes a front portion 122 of the insertion hole 121, a rear portion 123 of the insertion hole 121, and a middle portion 124 of the insertion hole 121.

The front portion 122 of the insertion hole 121 has an inner diameter allowing one end of the first needle 10 having a tube shape to be inserted therein.

The rear portion 123 of the insertion hole 121 has an inner diameter allowing an end portion of the second needle 110 having the slit 112 to be inserted therein.

The middle portion 124 of the insertion hole 121 is formed between the front portion 122 and the rear portion 123. The middle portion 124 may have an inner diameter smaller than an inner diameter of the front portion 122 or an inner diameter of the rear portion 123, and has a stop protrusion having a size by which the push rod 130 may be inserted.

In the positioning jig 120, a wedge-shaped portion 125 is formed in a rear end of the middle portion 124. The wedge-shaped portion 125 is configured to be press-fit to a sharp end portion of the second needle 110 in terms of shape and accommodate the sharp end portion of the second needle 110.

The push rod 130 serves to push the follicular unit of the second needle 110 toward an internal space 11 of the first needle 10. To this end, the push rod 130 is inserted into the needle interior 111 of the second needle 110.

The push rod 130 may be a solid bar or a rod-like component. However, in order to prevent an end of the push rod 130 from clinging to the follicular unit, the push rod 130 may have a dual structure. That is, having a dual structure, the push rod (not shown) may include a first outer push rod unit having a tube shape with a slit and a second inner push rod unit slidably inserted into an axial-directional hole of the outer push rod unit and formed as a solid shaft with a groove.

In this case, after any one of the first outer push rod unit and the second inner push rod unit may be moved to come into contact with the follicular unit, the other may come into contact therewith or not, and thus, a situation in which the end of the push rod 130 clings to the follicular unit may be effectively handled.

The push rod 130 may further include a groove 131 accommodating the hair member 22 of the follicular unit. Here, one end of the groove 131 is opened at the end of the push rod 130 facing the follicular unit. The groove 131 may be a space accommodating the hair member 22 such that the hair member 22 of the follicular unit may not be caught in a gap between the positioning jig 120 and the push rod 130.

A shape of the positioning jig 120 or the push rod 130 is not limited to the shape illustrated in FIG. 2. For example, as illustrated in FIGS. 8 through 12, the shape of the positioning jig 120 or the push rod 130 may be variously designed.

The positioning jig 120 facilitates a manual operation of inserting the follicular unit into the second needle 110.

The first instrument 100 may be operated in such a manner as illustrated in FIGS. 3 through 7.

FIGS. 3, 4, 5, 6, and 7 are cross-sectional views illustrating an operational principle of the first instrument illustrated in FIG. 2.

FIGS. 2, 3, 4, 5, 6 and 7 illustrate operation order of loading the follicular unit into a slitless first needle for hair implant.

Referring to FIG. 2, the follicular unit is prepared in the vicinity of the slit 112.

Figure 3:
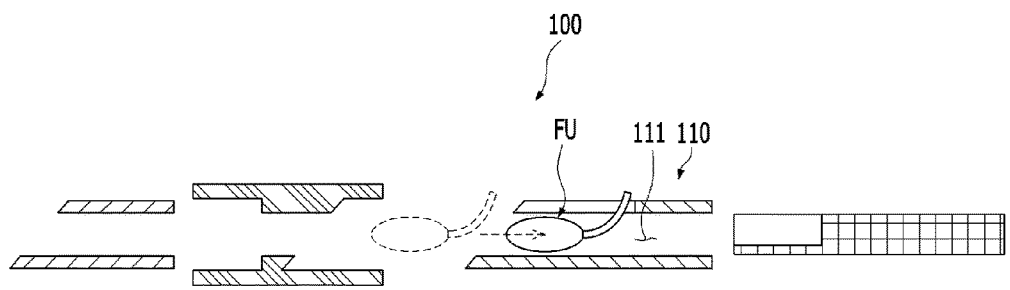
FIGS. 3 through 7 are cross-sectional views illustrating an operational principle of the first instrument illustrated in FIG. 2.

Referring to FIG. 3, the follicular unit is inserted into the needle interior 111 of the second needle 110 by a unit transportation tool such as a pincettes, or the like.

Figure 4:
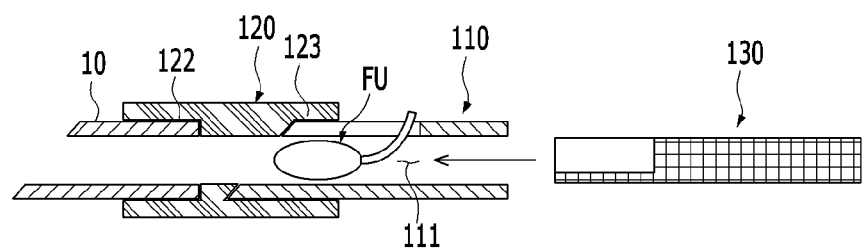

Referring to FIG. 4, the second needle 110 having a follicular unit is coupled to the rear portion 123 of the positioning jig 120, and the slitless first needle 10 is coupled to the front portion 122 of the positioning jig 120.

Figure 5:
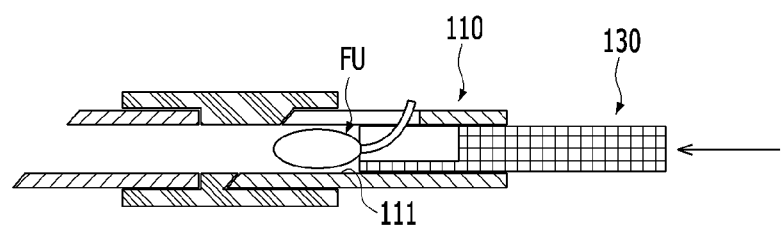

Referring to FIG. 5, the push rod 130 is disposed behind the second needle 110 and subsequently inserted into the needle interior 111 in a direction toward a front side of the second needle 100.

Figure 6:
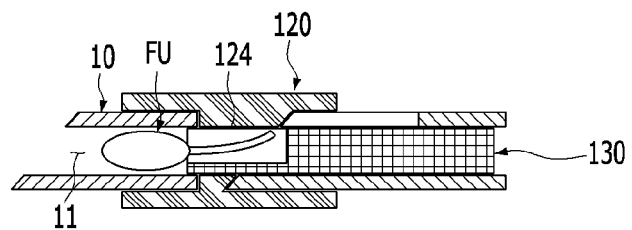

Referring to FIG. 6, the push rod 130 moves forwards. According to the movement of the push rod 130, the follicular unit moves from the needle interior 111, passing through the middle portion 124 of the positioning jig 120, to the internal space 11 of the first needle 10.

Figure 7:
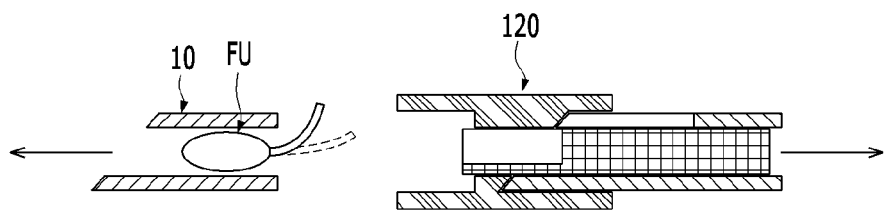

Referring to FIG. 7, the first needle 10 having the follicular unit is separated from the positioning jig 120.

The first needle 10 having the follicular unit may be loaded to a manual implanter (not shown) so as to be used, or may be loaded in plurality to a cartridge for an automated implanter.

FIGS. 8 through 12 are cross-sectional views illustrating application examples of a positioning jig or a push rod illustrated in FIG. 1.

Figure 8:
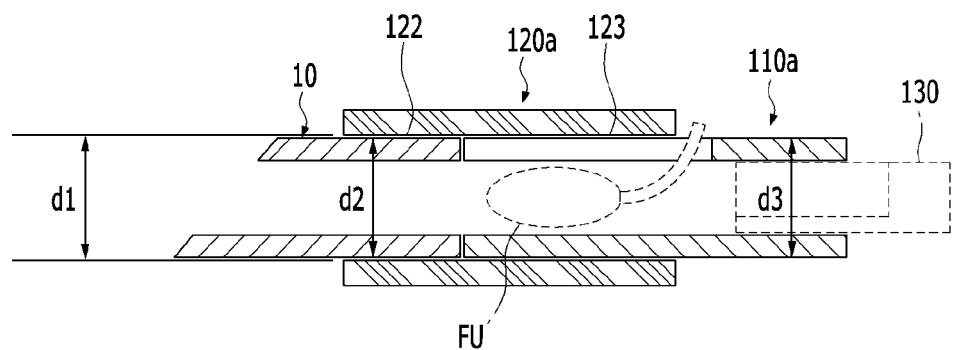
FIGS. 8 through 12 are cross-sectional views illustrating application examples of a positioning jig or a push rod illustrated in FIG. 1.

Referring to FIG. 8, a positioning jig 120a according to an application example of the present invention includes a front portion 122 of an insertion hole having an inner diameter d1 by which one end of the first needle 10 having a tube shape may be inserted and a rear portion 123 of an insertion hole having an inner diameter d1 by which a flat end portion of a second needle 110a having a slit is inserted. Here, the front end portion 122 and the rear end portion 123 of FIG. 8 are integrally connected, and the inner diameters d1 of the front portion 122 and the rear portion 123 are equal.

As illustrated in FIG. 8, an outer diameter d2 of the first needle 10 and an outer diameter d3 of the second needle 110a may be equal. Thus, the first needle 10 and the second needle 110a directly face each other and centers thereof may be aligned.

Also, when the follicular unit is moved, a connection portion of the components is reduced according to the method illustrated in FIGS. 1 through 7, reducing a possibility in which the hair bulb member of the follicular unit is damaged by burr.

Also, the follicular unit may be directly transmitted from the second needle 110a toward the first needle 10 by the push rod 130.

Figure 9:
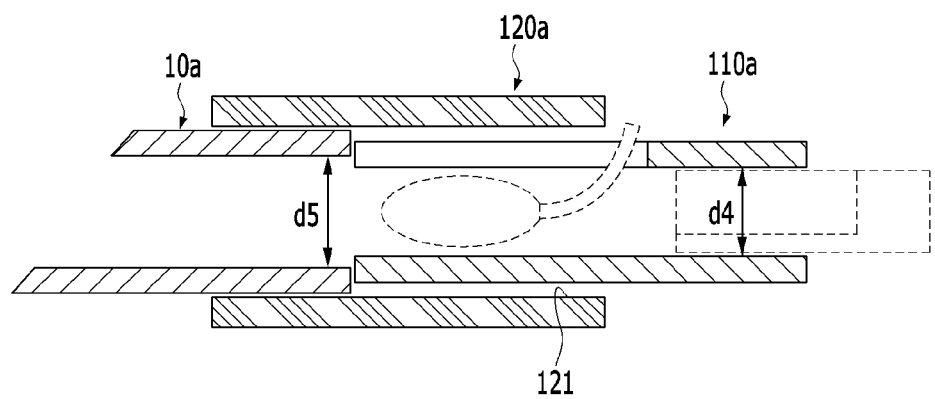

Referring to FIG. 9, an inner diameter d4 of the second needle 110a may be smaller than an inner diameter d5 of the first needle 10a.

When the follicular unit is moved, a possibility in which the hair bulb member of the follicular unit is damaged by burr of the connection portion of the components may be further reduced, compared with the method of FIG. 8.

Figure 10:
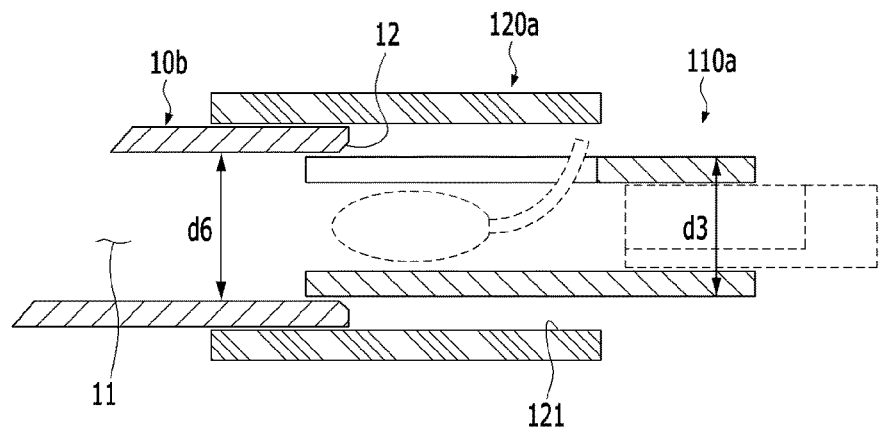

Referring to FIG. 10, an outer diameter d3 of the second needle 110a may be even smaller than an inner diameter d6 of a first needle 10b. In this case, the second needle 110a may be easily inserted into the insertion hole 121 of the positioning jig 120a and the internal space 11 of the first needle 10b.

A chamfer portion 12 is formed at the edge of the first needle 10b in the entrance of the internal space 11, allowing the second needle 110a to be more quickly and easily inserted into the internal space 11 of the first needle 10b.

Similar to the method of FIG. 10, when the follicular unit is moved, a possibility in which the hair bulb member of the follicular unit is damaged may be reduced.

Figure 11:
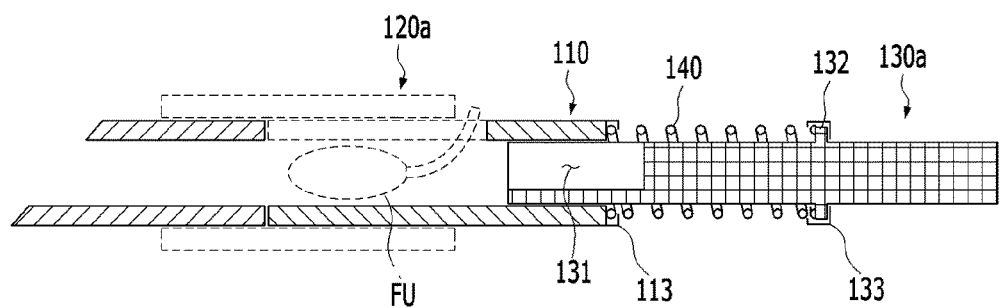

Referring to FIG. 11, the second needle 110 and a push rod 130a may be configured as a single combination body using elastic force of a spring 140.

For example, the push rod 130a further includes a spring support 132 formed to protrude from a portion spaced apart toward the opposite end of the follicular unit in a groove 131 and a spring 140 coupled between the spring support 132 and an end facing the follicular unit. One end of the spring 140 is in contact with a side of the spring support 132, and the other end of the spring 140 is in contact with an outer end of the second needle 110.

Also, one end of the spring 140 is fixed by a first fixture 133 of the spring support 132, and the other end of the spring 140 is fixed by a second fixture 113 at the outer end of the second needle 110.

The second needle 110 and the push rod 130a may be connected through the spring 140, and may be coupled to the positioning jig 120a immediately at a time.

A direction in which the second needle 110 and the push rod 130a are coupled is the same as a direction in which the push rod 130a moves forwards, and thus, as soon as the second needle 110 and the push rod 130a are coupled, movement force of the push rod 130a may be transmitted to the follicular unit. When the movement force applied to the push rod 130a is removed, the push rod 130a may be quickly returned to the original position by elastic repulsive force.

Figure 12:
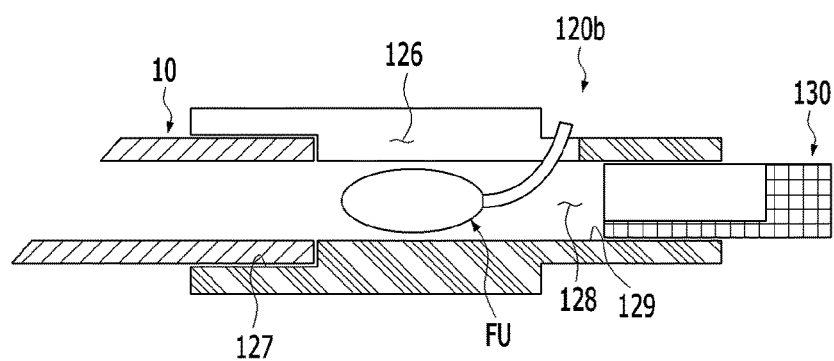

Referring to FIG. 12, a positioning jig 120b may be manufactured to have a new shape by incorporating the positioning jig 120 and the second needle 110 of FIG. 1.

The positioning jig 120b has a jig slit 126 and a front portion 127. The follicular unit to be transmitted toward the first needle 10 is disposed in the jig slit 126 within the jig, and one of the jig slit 126 is closed and the other side of the jig slit 126 is opened. One end of the first needle 10 having a tube shape is inserted into the front portion 127.

The positioning jig 120b includes a rear portion 129 integrally formed at the rear of the front portion 127 and having a guide hole 128 into which the push rod 130 is directly inserted. Here, an inner diameter of the guide hole 128 may be equal to or smaller than an inner diameter of the internal space 11 of the first needle 10.

Accordingly, upon receiving movement force of the push rod 130, the follicular unit of the positioning jig 120b may be smoothly, safely inserted toward the internal space 11 of the first needle 10.

Second Embodiment

An apparatus for loading a follicular unit into a needle for hair implant according to a second embodiment provides a second instrument using a pulling scheme modified from the pushing scheme of the first embodiment. When it is considered that the second instrument is smoothly able to load a follicular unit to the first needle, the first instrument may also form a group of the present invention together with the first instrument or various devices described hereinafter.

Figure 13:
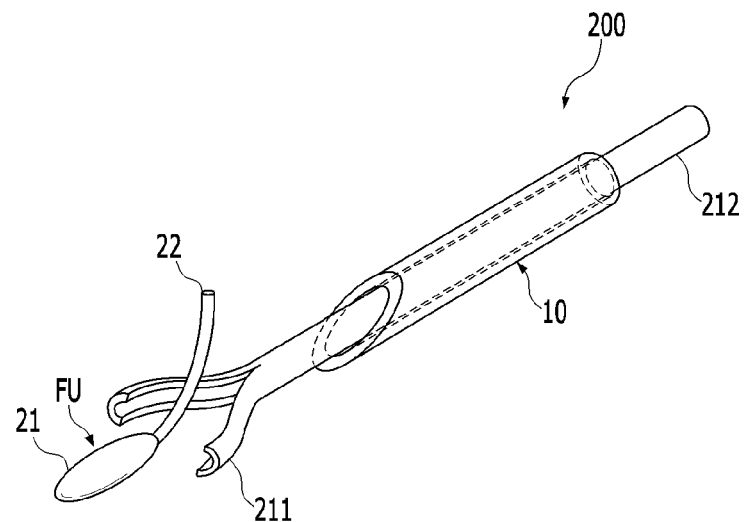
FIG. 13 is a perspective view illustrating a configuration of a second instrument of an apparatus for loading a follicular unit into a needle for hair implant according to a second embodiment of the present invention.
Figure 14:
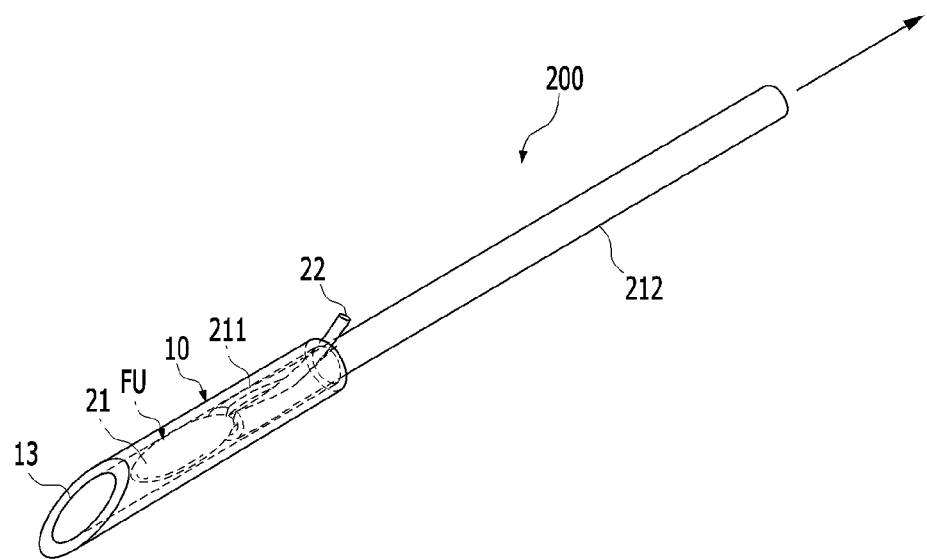
FIGS. 14 and 15 are perspective views illustrating an operational principle of the second instrument illustrated in FIG. 13.
Figure 15:
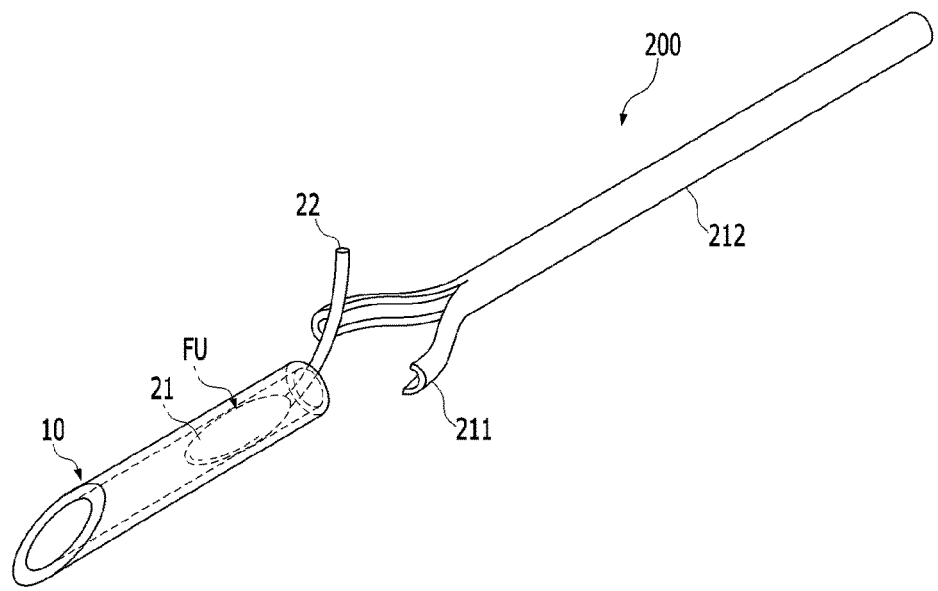
Figure 16:
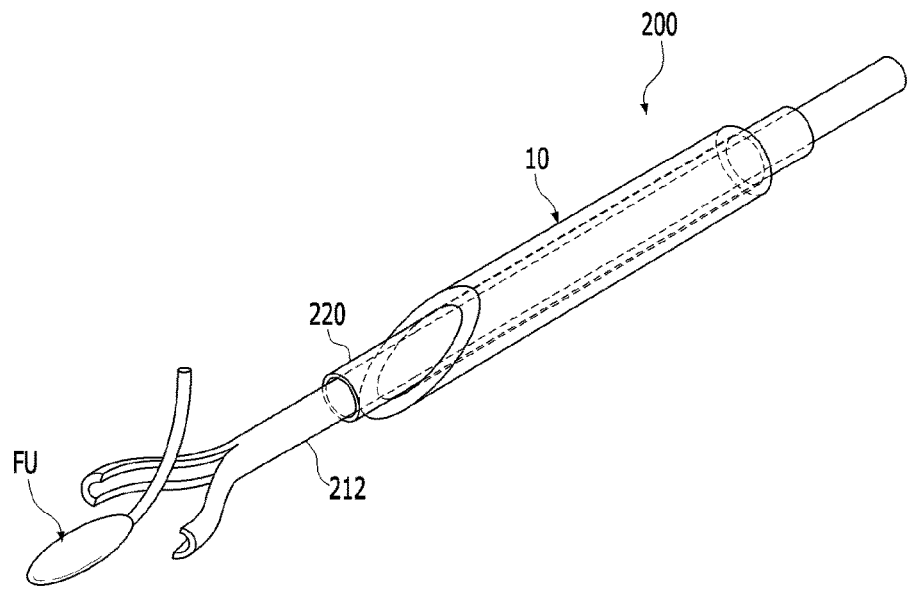
FIG. 16 is a perspective view illustrating an application example of the second instrument illustrated in FIG. 13.
Figure 17:
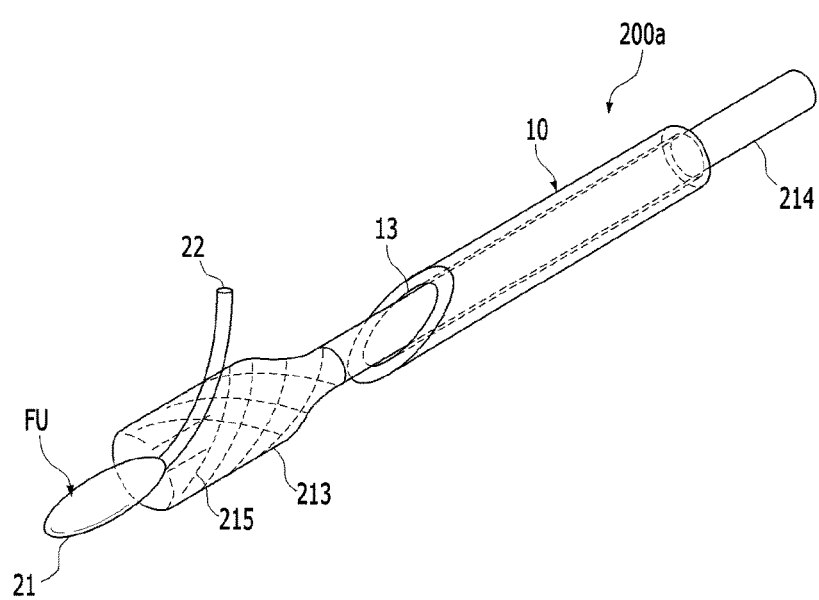
FIG. 17 is a perspective view illustrating another application example of the second instrument illustrated in FIG. 13.

FIG. 13 is a perspective view illustrating a configuration of a second instrument of an apparatus for loading a follicular unit into a needle for hair implant according to a second embodiment of the present invention, and FIGS. 14 and 15 are perspective views illustrating an operational principle of the second instrument illustrated in FIG. 13. FIG. 16 is a perspective view illustrating an application example of the second instrument illustrated in FIG. 13, and FIG. 17 is a perspective view illustrating another application example of the second instrument illustrated in FIG. 13.

Referring to FIG. 13, the apparatus for loading a follicular unit into a needle for hair implant according to the second embodiment of the present invention includes a slitless first needle 10. The other end of a hollow body of the first needle 10 has a sharp or wedge shape so as to pierce a transplantation region in a hair transplant procedure, and one end of the hollow body has a tubular shape to facilitate force transmission and an end surface of the one end is formed to be blunt.

Here, the other end of the first needle 10 has a sharp shape so as to be easily inserted into a scalp or a transplantation region.

Also, the apparatus for loading a follicular unit into a needle for hair implant according to the second embodiment of the present invention includes a second instrument 200 pulling a follicular unit toward the first needle 10 in order to load the follicular unit to the interior of the first needle 10.

The second instrument 200 is configured to insert a follicular unit into the first needle 10 for hair implant by using tweezers 211.

For example, the second instrument 200, a unit for gripping the follicular unit including a hair bulb member 21 having a diameter of a size movable within the first needle 10 and a hair member 22 extending from a rear end of the hair bulb member 21, includes the tweezers 211 having legs formed as an end portion thereof is bifurcated and a tweezer rod 212 having a diameter that may be inserted into the interior of the needle 10 and connected to the tweezers 211.

A position gripped by the tweezers 211 may correspond to the entirety of the hair member 22 or the hair bulb member 21 or a portion of the hair bulb member 21 according to a form or shape of the tweezers 211.

The tweezer rod 212 may be a hollow structure or a thin, fine tube structure with elasticity.

The tweezer rod 212 may be moved along an internal space of the first needle 10 by a person or an automated transportation device (not shown).

The tweezers 211 has elastic force on the basis of the tweezer rod 212.

The tweezers 211 may be manufactured by bisecting a front portion of the tweezer rod 212 as an elastic, thin tube structure and curbing the bisected portions. Here, a tweezer instrument structure (not shown) that may be mechanically operated using a wire, or the like, may also be applied to the present embodiment.

The tweezers 211 may have at least two legs. That is, the tweezers 211 may have two or four legs.

FIG. 13 illustrates a process of preparing to insert the follicular unit previously collected using the tweezers 211 into the first needle 10 for hair implant.

Here, the tweezer rod 212 is inserted in the internal space of the first needle 10 in advance. The tweezers 211 in an opened state may be positioned to grip the follicular unit.

FIG. 14 illustrates a process in which the tweezers 211 grips the hair member 22 of the follicular unit according to a backward movement of the tweezer rod 212, and the tweezer rod 212 moves backwards further so that the hair member 22 is inserted into the internal space of the first needle 10.

FIG. 15 illustrates a process in which the follicular unit is left within the first needle 10 and the tweezers 211 are removed to the outside.

During the process of FIGS. 13 and 14, outer surfaces of the tweezers 211 come into contact with a hole edge 13 of the first needle 10 as the tweezer rod 212 moves. Here, the tweezers 211 become narrower to be close to each other. Accordingly, the tweezers 211 grip the hair member 22 of the follicular unit.

As the tweezer rod 212 continues to move, the second instrument 200 pulls the hair member 22 and the hair bulb member 21 of the follicular unit into the first needle 10.

As a result, as illustrated in FIG. 15, the tweezer rod 212 and the tweezers 211 may be completely released out of the first needle 10. Here, as the tweezers 211 are expanded or returned to the original state, the tweezers 211 and the hair member 22 of the follicular unit are separated.

Thus, the hair bulb member 21 of the follicular unit is positioned in the internal space 11 of the first needle 10.

Referring to FIG. 16, the second instrument 200 may further include a guide tube 220 inserted into the tweezer rod 212 so as to be interposed between the tweezer rod 212 and the first needle 10, and rotatable or movable between the tweezer rod 212 and the first needle 10.

The guide tube 220 serves as the hole edge 13 of the first needle 10 illustrated in FIG. 14. The guide tube 220 may prevent damage to the hole edge 13 of the first needle 10 in advance.

The guide tube 220, while moving or rotating in the internal space of the first needle 10, may come into contact with an outer surface of the tweezers 211, and thus, the guide tube 220 may also serve to adjust an amount of expansion or contraction of the tweezers 211.

When the guide tube 220 first moves forwards, the tweezers 211 become narrower to grip the follicular unit. In this state, the guide tube 220, the tweezers 211, and the tweezer rod 212 move backwards. As a result, when the follicular unit reaches a position corresponding to the internal space of the first needle 10, the backward movement of the guide tube 220, the tweezers 211, and the tweezer rod 212 is stopped.

Thereafter, only the guide tube 220 is further moved in an outward direction from the internal space of the first needle 10.

Accordingly, the tweezers 211 are slightly opened in the internal space of the first needle 10, and as a result, the follicular unit is separated from the tweezers 211.

Thereafter, when the guide tube 220, the tweezers 211, and the tweezer rod 212 are completely removed from the internal space of the first needle 10, only the follicular unit is left in the internal space of the first needle 10. A shape of the tweezers 211 may not be limited to the illustrated shape. The number of the tweezers 211 may be two as illustrated in the drawing or more (for example, four legs).

Referring to FIG. 17, a second instrument 200a, a unit for gripping the follicular unit including a hair bulb member 21 having a diameter of a size movable within the first needle 10 and a hair member 22 extending from a rear end of the hair bulb member 21, includes a stent 213 having a mesh structure for gripping or releasing the hair member 22 and a stent rod 214 having a diameter that can be inserted into the interior of the first needle 10 and connected to the stent 213.

Here, the stent 213 may refer to a braided wire tube formed of a braided wire or a unit which is opened to be larger than a grip target and subsequently narrowed by an external force transmitted thereto to thus grip the target.

The stent rod 214 may be moved or rotated within the internal space of the first needle 10 by a person or an automated transportation device (not shown).

For example, an outer surface of the stent 213 may come into contact with the hole edge 13 of the first needle 10 according to movement of the stent rod 214, and the stent 213 may grip the hair member 22 of the follicular unit as a volume thereof is reduced.

That is, the stent rod 214 is inserted into the interior of the first needle 10 so as to be used. The stent rod 214 may move forwards or backwards in a length direction of the rod within the first needle 10, or may be rotated in a circumferential direction of the rod. The stent 213 is connected to the stent rod 214, and when the stent 213 is present outside of the first needle 10, a volume of the stent 213 expands, and when the stent 213 is present within the first needle 10, a volume thereof is reduced.

A recess 215 for receiving the hair member 22 or preventing damage to the hair member 22 may be further formed on the stent 213.

The stent 213 may be an elastic cylindrical mesh or lattice.

The instruments of the second embodiment or the previous first embodiment may be manufactured as mechanisms or robots for automatically loading the follicular unit into the slitless first needle and used in an automated hair transplant device or a robot.

Third Embodiment

An apparatus for loading a follicular unit into a needle for hair implant according to a third embodiment is similar to that of the second embodiment, but it provides a first device based on a scheme of pulling a follicular unit using intake pressure and loading the follicular unit into a first needle. The first device may also be able to smoothly load a plurality of follicular units into first needles, respectively.

Figure 18:
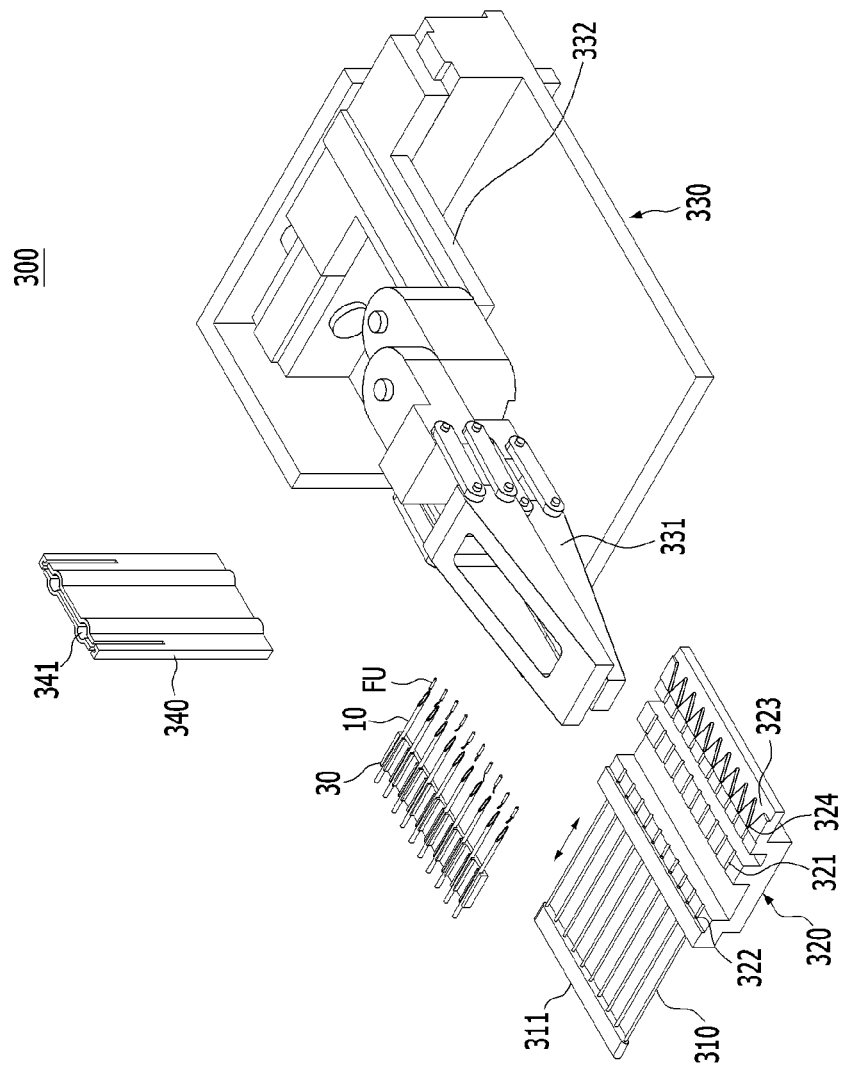
FIG. 18 is a perspective view illustrating a configuration of a first device of an apparatus for loading a follicular unit into a needle for hair implant according to a third embodiment of the present invention.

FIG. 18 is a perspective view illustrating a configuration of a first device of an apparatus for loading a follicular unit into a needle for hair implant according to a third embodiment of the present invention.

Referring to FIG. 18, a first device 300 includes a plurality of first needles 10 and intake tubes 310 corresponding to the number of the first needles 10.

A plurality of or a predetermined number of first needles 10 are mounted on a temporarily coupled spacer 30 to form a set.

The spacer 30 includes a plurality of mounting recesses disposed to be spaced apart from one another by a distance between the first needles 10. The spacer 30 is formed of rubber or an elastic material and temporarily fixes the first needles 10 by fractional contact. When the first needles 10 are mounted on a holder 320, the spacer 30 is separated from the first needles 10 by a person or by a separate clamp device (for example, refer to a fourth embodiment).

Follicular units are temporarily positioned in follicular unit mounting recesses 323 and loaded to the first needles 10 by the intake tube 310 as described hereinafter, respectively.

As mentioned above, the first needle 10 does not have a slit, and the other end of a hollow body of the first needle 10 has a wedge shape so as to be used in a transplantation region in a hair transplant procedure. One end of the hollow body has a tube shape and an end surface of the one end is formed to be blunt.

The intake tube 310 is configured to be movable toward the follicular unit mounting recesses 323.

One end of the intake pipe 310 is connected to a manifold or a header 311 to receive pneumatic pressure (for example, intake pressure) from the outside. The header 311 is connected to an external pneumatic device (not shown) through a hose or a connection tubular member.

The other end portion of the intake pipe 310 is insertedly or slidably coupled to an intake tube or a through hole 322 for tweezers of the holder 320.

The through hole 322 may also be used as a movement passage of tweezers, or the like, as described above.

The intake tube 310 is inserted into a needle interior of the first needle 10 in order to pull the follicular unit toward the first needle 10.

The intake tube 310 serves to adsorb the follicular unit with intake pressure generated by an external pneumatic device, that is, pressure lower than that of negative pressure or atmospheric pressure and serves to position the adsorbed follicular unit to the interior of the first needle 10 to correspond to a movement of the intake tube 310 by an automated transportation device (not shown).

The intake tube 310 may be replaced by the tweezers described above in the previous embodiment.

To this end, the first device 300 includes the holder 320, a gripper device 330, and a cartridge 340.

The cartridge 340 is a device storing the first needle 10 to be supplied to an automatic implanter (not shown).

The holder 320 has a plurality of needle mounting recesses 321 for disposing a plurality of first needles 10 or a set of first needles 10. The needle mounting recesses 321 are disposed to be spaced apart from one another in a length direction of the holder 320 on an upper surface of a body of the holder 320 and correspond to the number of the first needles 10. For example, the needle mounting recesses 321 of the holder 320 are a sort of needle setting portions providing a space in which the first needles 10 by unit (for example, ten or twenty needles per set) provided by a manufacturing factory (not shown) of the first needles 10.

The holder 320 includes a plurality of through holes 322 formed on one side with respect to the needle mounting recesses 321. The through holes 322 and a structure adjacent thereto serve as the positioning jig described above in the previous embodiment.

That is, the through holes 322 serve to align centers of the first needles 10 and the intake tubes 310 and guide sliding of the intake tubes 310.

The holder 320 has a plurality of follicular unit mounting recesses 323 formed on the other side with respect to the needle mounting recesses 321. The follicular unit mounting recesses 323 have a V shape based on a plane. An opened passage 324 is formed in a tip portion of the V shape. The opened passage 324 communicates with the needle mounting recess 321.

Thus, as the intake tubes 310 move forwards, ends of the intake tubes 310 pass through the through holes 322 of the holder 320, the internal spaces of the first needles 10 on the needle mounting recesses 321, and the opened passages 324 so as to be positioned in the internal spaces of the follicular unit mounting recesses 323, and as a result, the intake tubes 310 may close to the follicular units of the follicular unit mounting recesses 323.

Here, when intake pressure is applied to the intake tubes 310, the intake tubes adsorb the follicular units of the follicular unit mounting recesses 323 by the intake pressure.

Thereafter, as the intake tubes 310 moves backwards, the follicular units adsorbed to the ends of the intake tubes 310 pass through the opened passages 324 from the follicular unit mounting recesses 323 so as to be positioned in the internal spaces of the first needles 10 on the needle mounting recesses 321.

Thereafter, when the intake pressure is removed from the intake tubes 310, the follicular units are separated from the ends of the intake tubes 310 in the internal spaces of the first needles. As a result, the follicular units are positioned in the needle interior of the first needles 10, that is, loaded.

Subsequently, the intake tubes 310 move backwards, and as a result, ends of the intake pipes 310 are released from the internal spaces of the first needles 10 and returned to the original positions of the through holes 322.

The gripper device 330 has a robot or a mechanism for gripping the first needles 10 with the follicular units loaded therein from the holder 320 and transferring the first needles 10 to the interior of the cartridge 340.

The gripper device 330 includes a gripper 331 simultaneously gripping the first needles 10 placed on the plurality of needle mounting recesses 31 of the holder 320 and a multi-axis transportation device 332 transporting the gripper 331 through multi-degree of freedom operation controlling between the holder 320 and the cartridge 340.

The cartridge 340 may be disposed such that a needle entrance 341 is oriented upwards. The gripper 331 and the first needles 10 are positioned above the needle entrance 341 of the cartridge 340 by the multi-axis transportation device 332. Thereafter, through a releasing operation of the gripper 331, the first needles 10 are separated from the gripper 331 and dropped to be loaded into the cartridge 340 through the needle entrance 341 of the cartridge 340.

The multi-axis transportation device 332 is manufactured in the form of a robot or a mechanism implemented by a sort of factory automation (FA). For example, the multi-axis transportation device 332 may include a control unit, a power unit, and an instrument unit. The control unit is a part providing a command to the power unit and includes hardware and software required for performing controlling. Hardware may include a microprogrammed control unit (MCU) and a motor controller including software, a control panel for a user environment, a button, a pedal, and the like. The power unit is a part providing power to the instrument unit according to a command from the control unit and may include a motor and a power supply. In order to operate the tweezers 211 for gripping the follicular unit and the gripper 331 for gripping the first needle 10 by pneumatic pressure, a vacuum compressor, a solenoid valve, and the like, may be additionally provided to the power unit.

For example, the first device 300 may be operated as follows.

That is, a user input by a button or a pedal may be required to start and terminate some operations.

The first device 300 prepares to mount the cartridge 340 in a mounting position such as a cartridge mounting/dismounting block (not shown), or the like.

In a follow-up operation, the first needle 10 is mounted on the needle mounting recess 321. If necessary, the spacer 30 may be removed from the first needle 10.

The gripper 331 operates to press the first needle 10 toward the holder 320 to temporarily fix the first needle 10 to the needle mounting recess 321 of the holder 320. If necessary, the first needle 10 may also be moved to be tightly attached to the through hole 322 according to a horizontal movement of the gripper 331.

The first device 300 cause the tweezers (not shown) or the intake tube 310 to be inserted into and pass through the first needle 10 and move forwards up to the follicular unit mounting recess 323.

If necessary, in order to change a direction of the follicular unit mounting recess 323 to an upward direction, the holder 320, the gripper 331, the gripper device 330, and the cartridge 340 may be rotated.

The follicular unit is positioned on the follicular unit mounting recess 323 and a gripping operation is performed by the tweezers or the intake tube 310.

Thereafter, the tweezers or the intake tube 310 moves backwards and as a result, the follicular unit enters the interior of the first needle 10, and in this state, the gripped follicular unit is released.

Thereafter, the tweezers or the intake tube 310 completely moves back out of the first needle 10 so as to be removed.

The gripper device 330 transports the first needle 10 from the holder 320 to the cartridge 340 and subsequently inserts the first needle 10 into the cartridge 340.

Fourth Embodiment

An apparatus for loading a follicular unit into a needle for hair implant according to a fourth embodiment is similar to that of the third embodiment, but it provides a second device sweeping first needles into a cartridge using a sweeper. The second device may also be able to load a follicular unit into an internal space of the first needle in a pulling manner.

Figure 19:
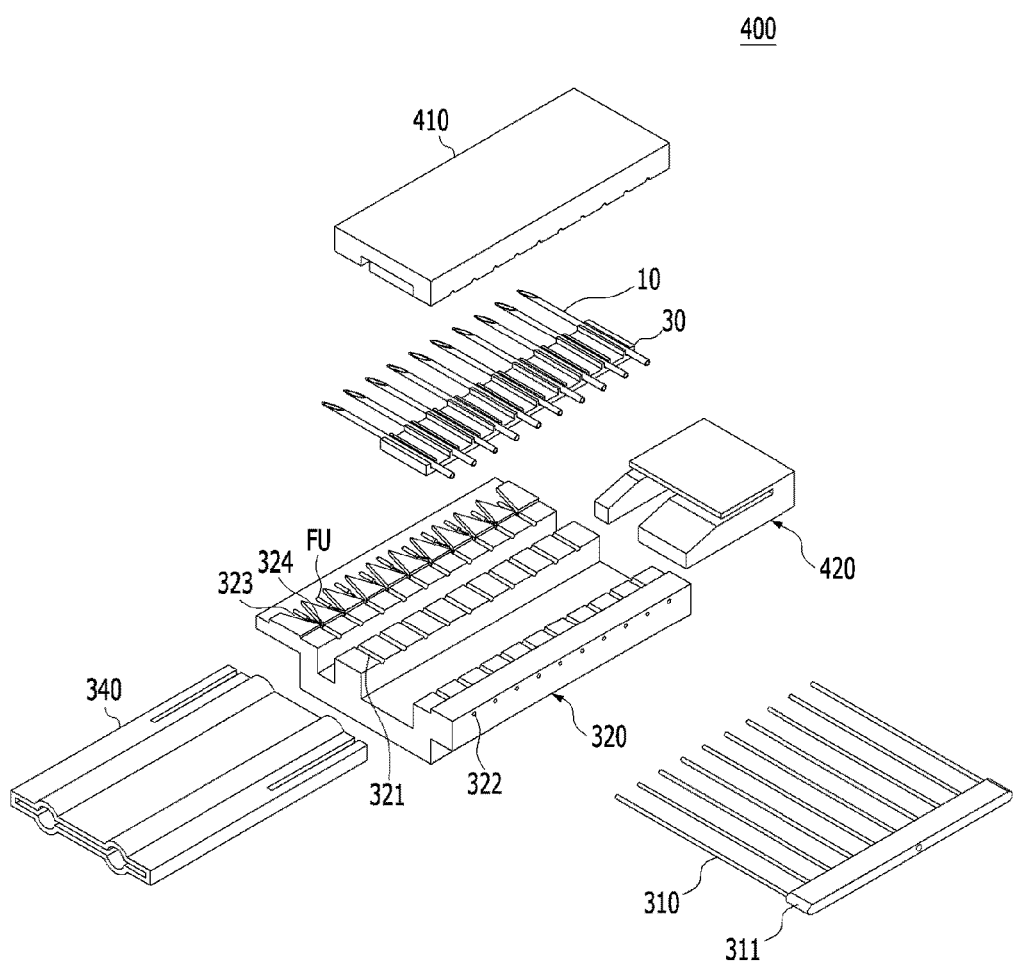
FIG. 19 is a perspective view illustrating a configuration of a second device of an apparatus for loading a follicular unit into a needle for hair implant according to a fourth embodiment of the present invention.

FIG. 19 is a perspective view illustrating a configuration of a second device of an apparatus for loading a follicular unit into a needle for hair implant according to a fourth embodiment of the present invention.

Referring to FIG. 19, a second device 400 includes a holder 320 having a needle mounting recess 321, a through hole 322, a follicular unit mounting recess 323, and an opened passage 324.

The second device 400 includes the intake tube 310 and the header 311 as described above. The intake tube 310 may be replaced by tweezers.

The second device 400 includes a cartridge 340 disposed to be parallel to the holder 320.

The second device 400 includes a clamp device 410 pushing a spacer 30 temporarily coupled to the first needle 10 downwards to separate the first needle 10 from the spacer 30, and temporarily fix the first needle 10 to the holder 320.

The second device 400 includes a sweeper 420 (please refer to the descriptions with reference to FIGS. 26 through 31) disposed in a direction opposite to the cartridge 340, that is, on the other side of the holder 320, and sweeping the first needles 10 positioned on the needle mounting recesses 321 into the cartridge 340.

Operation order of the second device 400 is as follows.

The second device 400 prepares to install the cartridge 300 in a mounting position such as a cartridge mounting/dismounting block (not shown), or the like.

The first needle 10 and the spacer 30 are mounted on the holder 320.

The clamp device 410 performs a downward operation, and thus, the needle 10 is fixed to the needle mounting recess 321 of the holder 320 and the spacer 30 is simultaneously removed.

The second device 400 inserts the tweezers or the intake tube 310 into the first needle 10 through the through hole 322 of the holder 320, and moves the tweezers or the intake tube 310 forwards up to the follicular unit mounting recess 323.

The tweezers or the intake tube 310 grips the follicular unit of the follicular unit mounting recess 323.

Moving backwards, the tweezers or the intake tube 310 puts down the follicular unit from the interior of the first needle 10, and further moves backwards so as to be removed to the outside of the first needle 10.

The clamp device 410 operates upwards so as to be removed from the first needle 10 in the upward direction.

The second device 400 moves the sweeper 420 forwards to sweep the first needles 10 into an internal space of the sweeper 420 and, at this time, the spacer 30 may also be subsequently discharged to the outside of the holder 320.

The second device 400 continues to move the sweeper 420 forwards to insert the first needles 10 into the cartridge 340.

A specific process of sweeping the first needles 10 by the sweeper 420 and inserting the first needles 10 into the cartridge 340 may be described in detail in a fifth embodiment hereinafter with reference to FIGS. 26 through 31.

Fifth Embodiment

An apparatus for loading a follicular unit into a needle for hair implant according to a fifth embodiment is similar to that of the first embodiment, and provides a third device aligning centers of a first needle and a second needle by a positioning jig and subsequently pushing a follicular unit of the second needle toward the first needle by a push rod inserted into the second needle to resultantly load the follicular unit to an internal space of the first needle. The third device may also smoothly load a plurality of follicular units into the first needles, respectively. In the fifth embodiment, similar reference numerals are given to components which are the same as or similar to those of the components described above in the previous embodiments, and redundant descriptions may be omitted.

Figure 20:
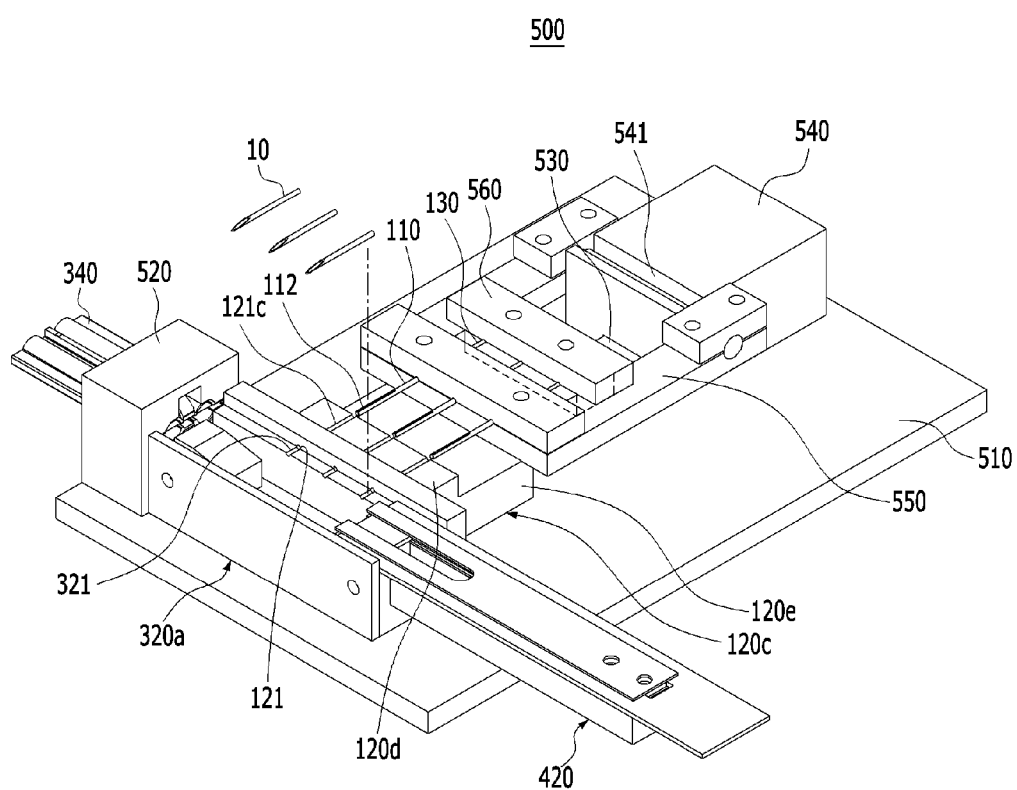
FIG. 20 is a perspective view illustrating a configuration of a third device of an apparatus for loading a follicular unit into a needle for hair implant according to a fifth embodiment of the present invention.

FIG. 20 is a perspective view illustrating a configuration of a third device of an apparatus for loading a follicular unit into a needle for hair implant according to a fifth embodiment of the present invention, and FIGS. 21 through 25 are perspective views illustrating an operating method of the third device illustrated in FIG. 20.

Figure 21:
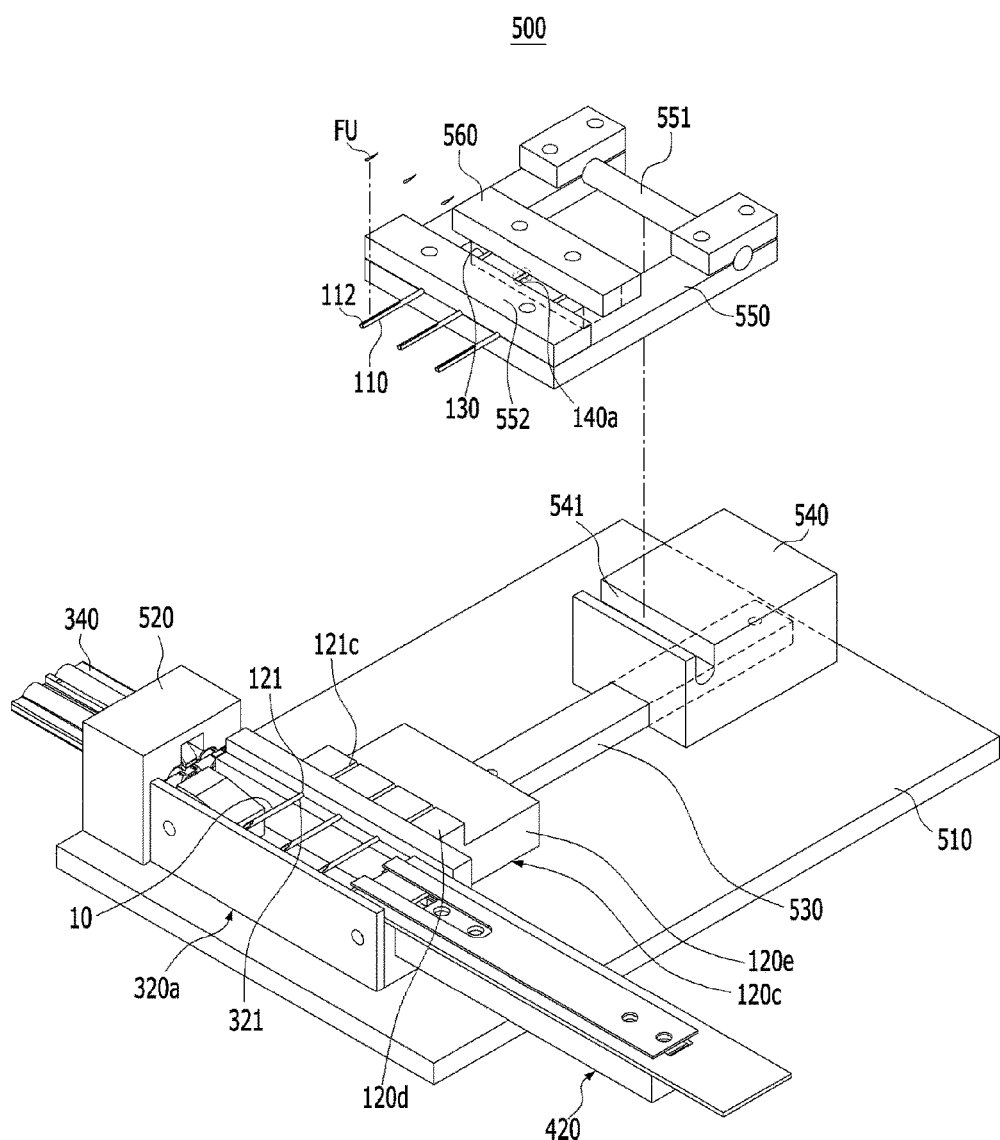
FIGS. 21 through 25 are perspective views illustrating an operating method of the third device illustrated in FIG. 20.

Referring to FIG. 20 or 21, a significant difference of the third device from the devices of the previous embodiments is a scheme of loading a follicular unit into the first needle 10.

That is, the first device and the second device use the tweezers or the intake tube, whereas the third device 500 loads the follicular unit into the first needle 10 using the second needle 110 with a slit 112 as a relay unit.

That is, the third device refers to a unit for pulling the follicular unit toward the first needle 10 and inserting the follicular unit into the first needle 10, instead of the first device or the second device.

To this end, the third device 500 includes a base plate 510, a holder 320a, a cartridge mounting/dismounting block 520, a sweeper 420, a positioning jig 120c, a guide rail 530, a moving block 540, a first moving frame 550, and a second moving frame 560.

The base plate 510 is an installation frame or a support frame of the third device 500.

In order to dispose a plurality of first needles 10, the holder 320a is installed on the base plate 510. The holder 320a have a plurality of needle mounting recesses 321 for displaying a plurality of first needles 10, and a plurality of insertion holes 121 are each formed to be aligned with the center of each of the needle mounting recesses 321 on one side with respect to the needle mounting recesses 321.

The cartridge mounting/dismounting block 520 is installed on the base plate 510 and tightly attached to an outer surface of the holder 320a in a length direction. The cartridge 340 is inserted into a cartridge insertion hole of the cartridge mounting/dismounting block 520.

The sweeper 420 is coupled to be slidable on the holder 320a. The sweeper 420 serves to sweep the first needles 10 positioned on the needle mounting recesses 321 of the holder 320a into the interior of the cartridge 340.

The positioning jig 120c is disposed on the base plate 510 and tightly attached to a rear surface of the holder. The positioning jig 120c have a plurality of guide grooves 121c formed in an extending direction of the insertion hole 121 of the holder 320a to guide movement of the second needle 110.

The positioning jig 120c is a stair structure including an upper portion 120d on which the guide grooves 121c are formed and a lower portion 120e formed to be lower than the upper portion 120d and having a guide surface supporting sliding of the first movement frame 550.

The guide rail 530 is disposed in a direction perpendicular to a length direction of the holder 320a, installed on the base plate 510, and extends backwards of the positioning jig 120c. The guide rail 530 is a rail part of a linear module (LM).

The moving block 540, a moving part of the linear module, is coupled to the guide rail 530 to move along the guide rail 530.

The first moving frame 550 is rotatably coupled to a hinge recess 541 of the moving block 540.

In detail, a shaft 551 (please refer to FIG. 21) of the first moving frame 550 is rotatably coupled to the hinge recess 541 of the moving block 540.

The first moving frame 550 serves to move the second needle 110 through the insertion hole 121 of the holder 320a such that the second needle 110 is aligned with the first needle 10.

The plurality of second needles 110 are installed in front of the first moving frame 550.

The follicular unit is loaded into the needle interior of the second needle 110 through the slit 112 of the second needle 110. Here, a user grips the follicular unit with pincettes and places the follicular unit in the needle interior of the second needle 110.

The insertion hole 121 of the holder 320a penetrates through a wall of the holder 320a toward the guide groove 121c of the positioning jig 120c.

One end portion of each of the push rods 130 is inserted into the plurality of second needles 110.

The other end portions of the push rods 130 are installed in front of the second moving frame 560.

The second moving frame 560 is a moving part disposed between both bodies of the first moving frame 550 and using the both bodies as rails.

Here, both end portions of the second moving frame 560, as a linear guide moving part having recesses that can be inserted into both bodies of the first moving frame 550, are configured to be slidably moved in a length direction of the body bodies of the first moving frame 550.

The second moving frame 560 serves to move the push rod 130 positioned within the second needle 110 on the basis of the first moving frame 550.

As a result, the push rod 130 pushes the follicular unit of the second needle 110 so that the follicular unit is loaded into the first needle 10.

Here, in order to implement movement of the moving block 540 and the first moving frame 550 in an automated manner, a total of two actuators, including an actuator for moving the moving block 540 and an actuator for moving the second frame 560, may be used.

However, although not shown, according to a modified example of the third device 500, the moving block 540 may be removed so a function of separating, rotating, and coupling the moving block 540 and the first moving frame 550 is eliminated, but the third device may be configured to be mechanically simpler and operated by a force of a single actuator.

For example, the modified example of the third device 500 will be described with reference to FIG. 21. Here, an actuator (not shown) such as a power cylinder device maybe used instead of the moving block 540.

Here, an actuator may be disposed between a rear portion of the second moving frame 560 and a front portion of a shaft 551 of a first moving frame 550. Also, a moving rod of the actuator may be connected to a rear portion of the second moving frame 560. A housing of the actuator may be installed on and supported by the base plate 510.

The first moving frame 550 may be coupled to the guide rail 530 so as to be moved along the guide rail 530 through a change in design.

A power transmission spring 140a may be interposed between a rear surface of the front portion 552 of the first moving frame 550 and a front side of the second moving frame 560. The spring 140a may be inserted into the push rod 130.

A front end of the spring 140a may be in contact with a rear surface of the front portion 552 of the first moving frame 550, and a rear end of the spring 140a may be in contact with a front surface of the second moving frame 560.

When a moving rod of the actuator positioned behind the second moving frame 560 pushes the second moving frame 560 to move the second moving frame 560 (for example, move it forwards), movement force of the moving rod is transmitted to the first moving frame 550 through the spring 140a.

Accordingly, the first moving frame 550, the spring 140a, and the second moving frame 560 are simultaneously moved, and thereafter, when the front portion of the first moving frame 550 reaches a rear side of the upper end portion 120d of the positioning jig 120c, the first moving frame 550 may be stopped. At this time, the actuator further moves the moving rod by a predetermined stroke. Accordingly, the spring 140a is compressed, and the second moving frame 560 may be further moved by the compressed distance.

That is, the modified example of the third device 5000 may be configured such that the spring 140a for power transmission is interposed between the rear surface of the front portion 552 of the first moving frame 550 and the front surface of the second moving frame 560, and operations of the first moving frame 550 and the second moving frame 560 sequentially performed by an operation of the single actuator.

Also, although not shown, like rotational force is converted into linear reciprocating force by a robot or a mechanism that can be implemented by a factory automation technology, the sweeper 420, the first moving frame 550, and the second moving frame 560 may be configured to be movable automatically or semi-automatically by rotational force of a motor or an operational force of the actuator.

Hereinafter, an operation method of the third device will be described with reference to FIGS. 21 through 25.

Referring to FIG. 21, the third device 500 is prepared such that the cartridge 340 is inserted and temporarily fixed to the cartridge insertion hole of the cartridge mounting/dismounting block 520.

The first needle 10 is mounted on the needle mounting recess 321 of the holder 320a. Here, the first needle 10 may be maintained in a state of being temporarily fixed by a clamp device (not shown) (for example, the clamp device 410 of FIG. 19).

A follicular unit may be loaded to the interior of the second needle 110 through the slit 112 of the second needle 110.

Figure 22:
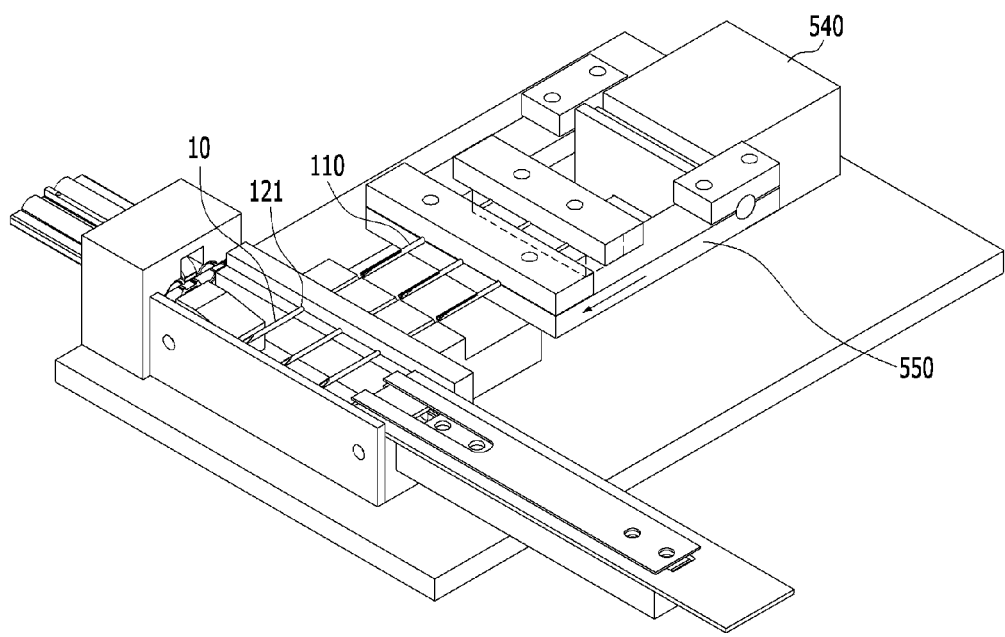

The first moving frame 550 in a state illustrated in FIG. 21 is coupled to the moving block 540 as illustrated in the state of FIG. 22.

Figure 23:
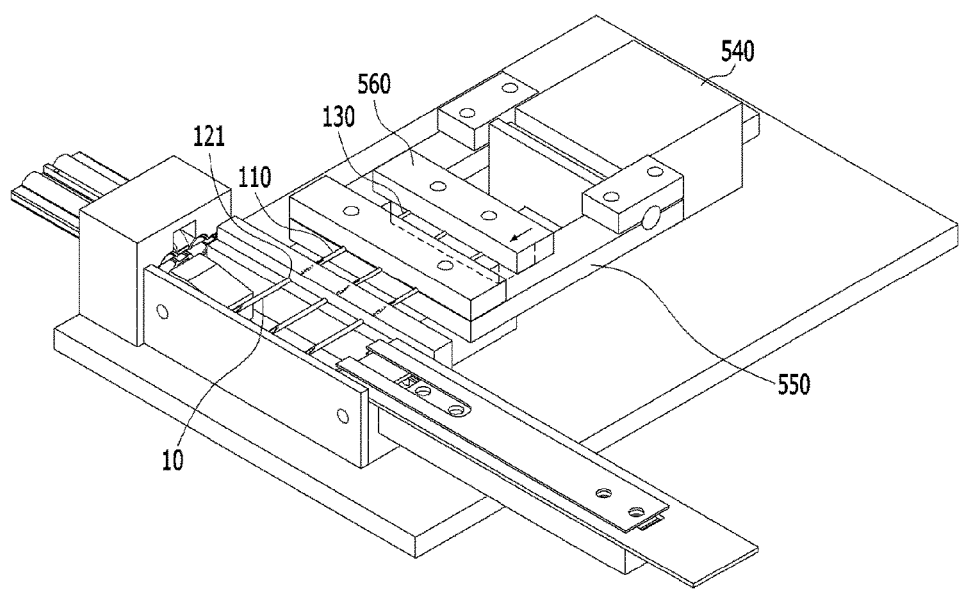

Referring to FIG. 23, as the moving block 540 and the first moving frame 550 move forwards, the second needle 110 is tightly attached to the first needle 110 within the insertion hole 121.

Figure 24:
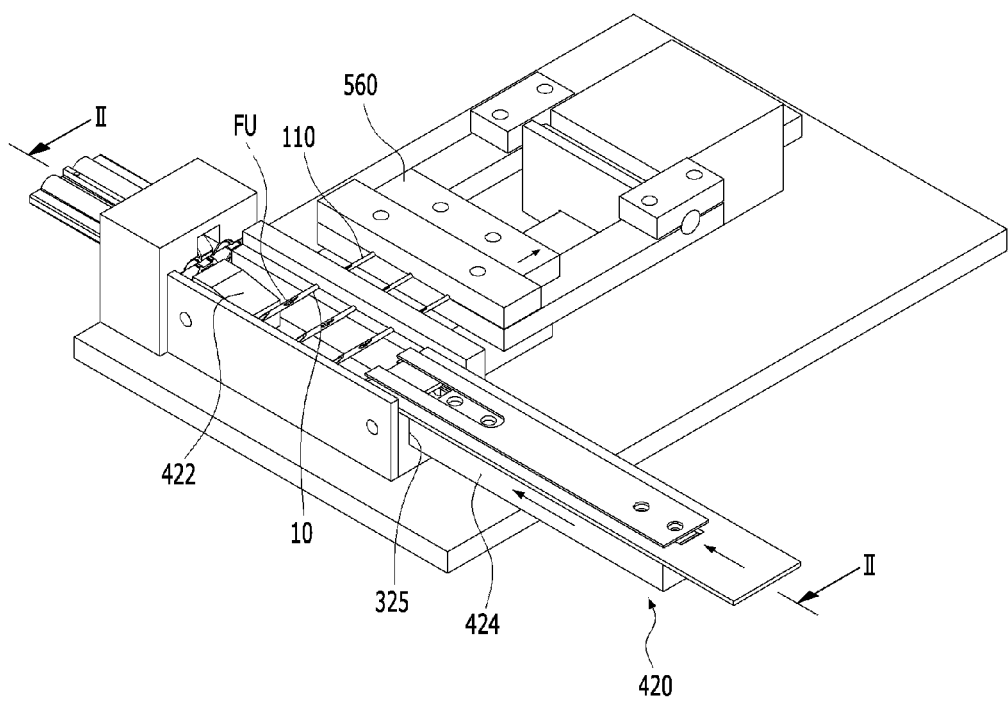

Referring to FIG. 24, in a state in which the moving block 540 and the first moving frame 550 are stopped, the second moving frame 560 moves forwards. As a result, the push rod 130 moves forward, and the follicular unit within the second needle 110 is transmitted to the interior of the first needle 10. That is, the follicular unit is loaded.

Figure 25:
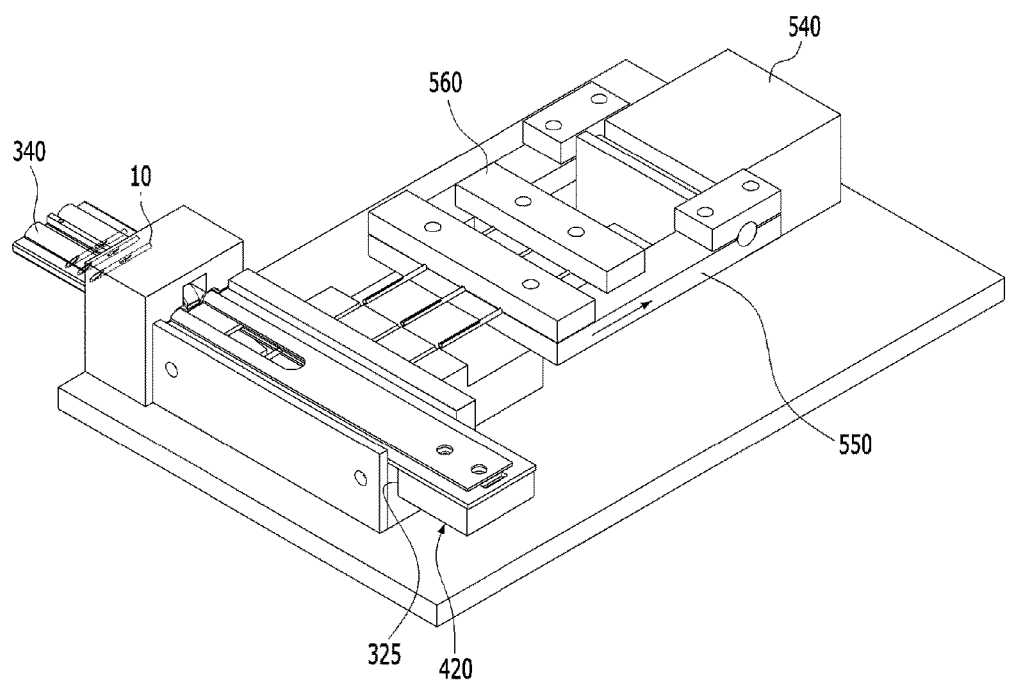

Referring to FIG. 25, the moving block 540, the first moving frame 550, and the second moving frame 560 move backwards, the clamp device (not shown) (for example, the clamp device 410 of FIG. 19) is removed upwards.

The sweeper 420 sweeps the first needle 10 and moves toward the cartridge 340, and a push plate of the sweeper 420 moves forward to insert the first needle 10 to the interior of the cartridge 340.

Hereinafter, a specific operation of the sweeper 420 will be described.

FIGS. 26 through 31 are cross-sectional views illustrating an operating method of a sweeper, taken along line II-II of FIG. 24.

Figure 26:
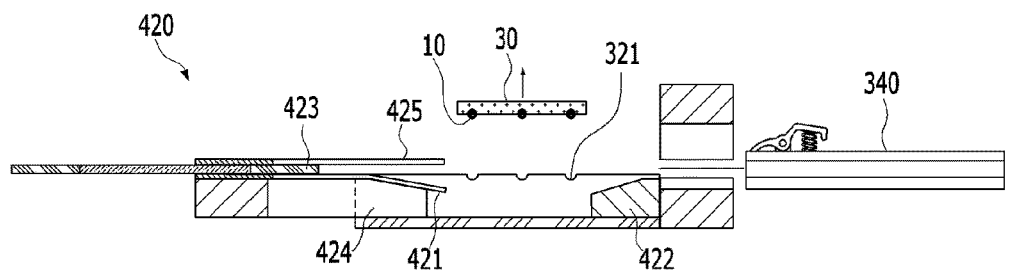
FIGS. 26 through 31 are cross-sectional views illustrating an operating method of a sweeper, taken along line II-II of FIG. 24.
Figure 27:
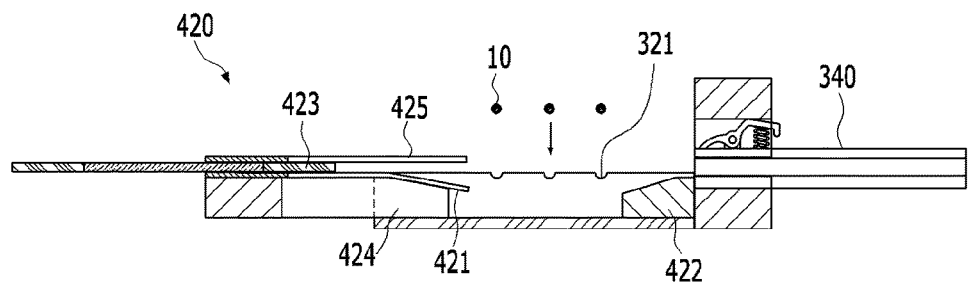
Figure 28:
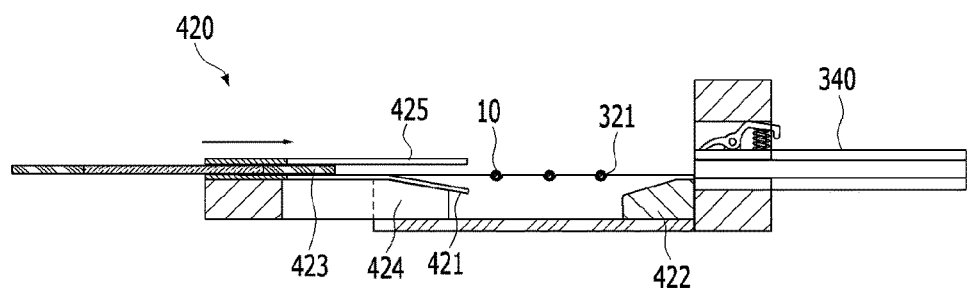

Referring to FIGS. 26, 27, and 28, the spacer 30 is separated from the first needle 10, and the first needle 10 is mounted on the needle mounting recess 321.

The sweeper 420 is configured to perform an operation of sweeping the slitless first needle 10 and inserting the sweeped first needle 10 into the cartridge 340. For example, the sweeper 420 sweeps the first needle 10 by lifting up the first needle 10 from the needle mounting recess 321 by using a lift plate 421 and a lift block 422 of the sweeper 420 having elastic force, and pushes the first needle 10 in a direction toward the cartridge 340 to insert, that is, load, the first needle 10 into the interior of the cartridge 340.

Here, the lift plate 421 has an end portion bent downwards to correspond to a shape of an upper surface of the support block 424.

The sweeper 420 includes a push plate 423 slidably coupled between the lift plate 421 and the guide plate 425 and a support block 424 disposed below the lift plate 421 and movably coupled to a sliding hole 325 (please refer to FIG. 24) of the holder 320a.

Figure 29:
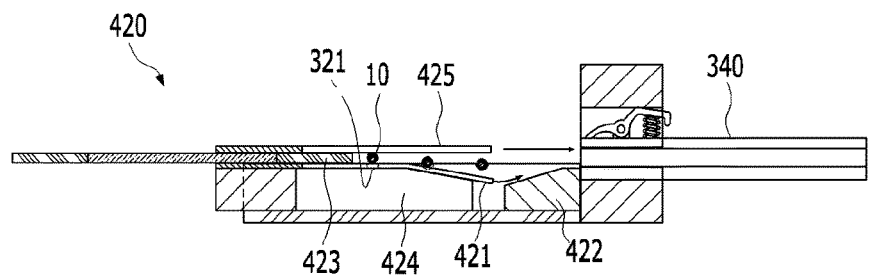

When the sweeper 420 starts to operate in a state illustrated in FIG. 28, the lift plate 421, the push plate 423, the support block 424, and the guide plate 425 move toward the lift block 422 as illustrated in FIG. 29.

The lift plate 421 moving forwards performs an operation of sequentially taking the first needle 10 out of the needle mounting recess 321 or sweeping the first needle 10. That is, a sloped surface of the downwardly bent end portion of the lift plate 421 meets the first needle 10 to resultantly perform an operation of drawing up the first needle 10 from the needle mounting recess 321.

As a result, the first needle 10 is separated from the needle mounting recess 321 and placed between the lift plate 421 and the guide plate 425.

Figure 30:
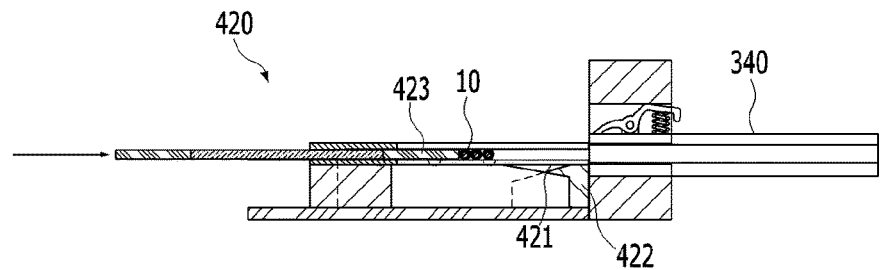

Referring to FIG. 30, an end portion of the lift plate 421 meets a sloped surface of the lift block 422 to be spread to serve as a connecting bridge allowing the first needle 10 and the push plate 423 to move toward the cartridge 340.

Figure 31:
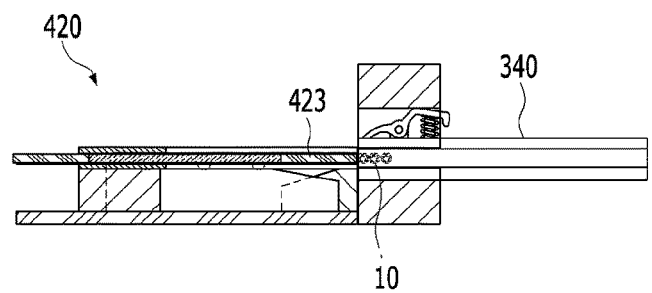

Referring to FIG. 31, the push plate 423 moves forwards. Such an operation is an operation of pushing the first needle 10 to the side by the push plate 423. As a result, the first needle 10 is inserted into the cartridge 340.

Figure 32:
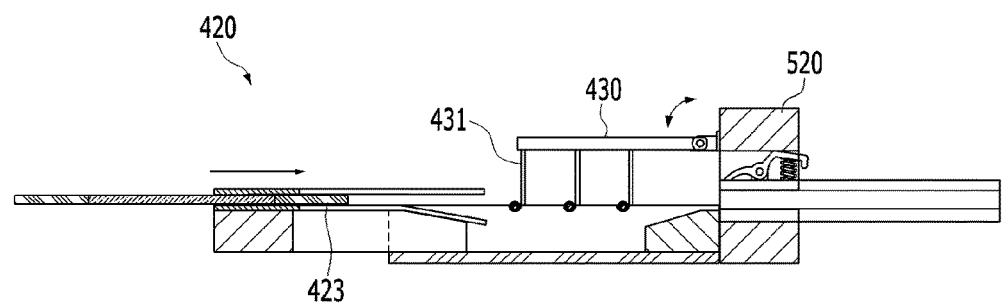
FIGS. 32 and 33 are cross-sectional views illustrating an application example of the sweeper illustrated in FIG. 27.
Figure 33:
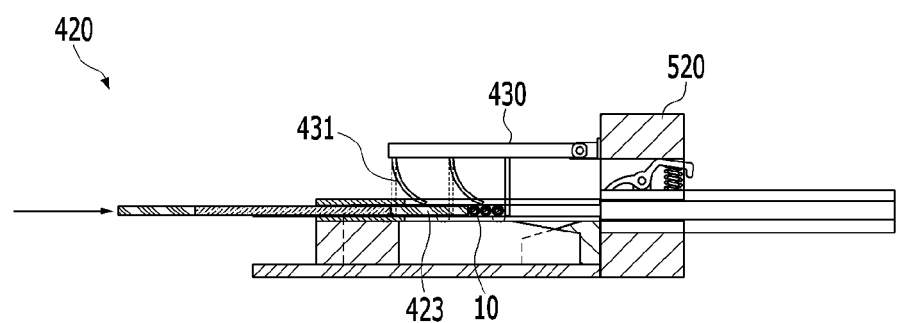

FIGS. 32 and 33 are cross-sectional views illustrating an application example of the sweeper illustrated in FIG. 27.

Referring to FIGS. 32 and 33, the sweeper 420 includes a foldable support 430 coupled to the cartridge mounting/dismounting block 520 and disposed above the first needle by a hinge operation and a plurality of needle anti-torsion elastic wires 431 connected to a lower surface of the foldable support 430 and disposed above the first needle. Here, the elastic wires 431 may be replaced by a ribbon, a fixture, or an elastic member.

A lower end portion of the elastic wire 431 is in contact with the first needle 10 on the back of the first needle 10 to serve to prevent the first needle 10 pushed by the push plate 423 to be moved from being in disorder in zigzags, or the like.

Figure 34:
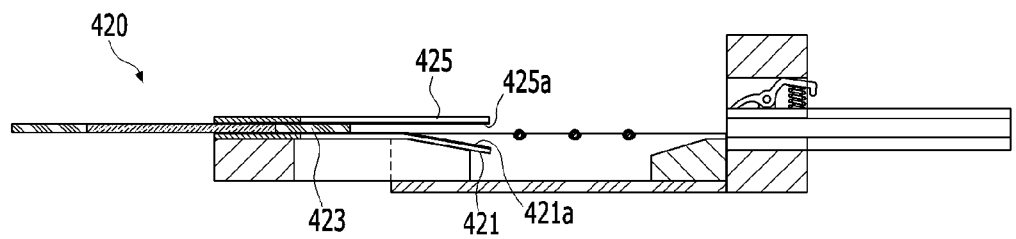
FIG. 34 is a cross-sectional view illustrating another application example of the sweeper illustrated in FIG. 27.

FIG. 34 is a cross-sectional view illustrating another application example of the sweeper illustrated in FIG. 27.

Referring to FIG. 34, in the sweeper 420, frictional contact pad layers 421a and 425a are respectively formed on a lower surface of the guide plate 421 and an upper surface of the lift plate 421 in order to prevent the first needle 10 from being in disorder through frictional contact with the first needle 10.

The frictional contact pad layers 421a and 425a may be formed of a soft pad material such as a soft synthetic resin or felt, and serve to guide the first needle 10 in a state of being pushed to be transferred from being distorted during transfer.

Also, in the present embodiment, the sweeper 420 may be coupled to a holder (not shown) with a serrated cross-section so as to be used as a transfer method for preventing the first needle 10 from being in disorder. Here, the holder having a serrated cross-section helps the first needle 10 pushed to be moved by the push plate 423 to pass over serration from one valley between serrations to move to the other valley. Thus, the first needle 10 may be moved, while being automatically aligned in posture through the valley between serrations.

Also, in the fifth embodiment, a needle-transferring timing belt (not shown) may be used instead of the sweeper 420. Here, the needle-transferring timing belt has an attachment in each of a plurality of protrusions to transfer the first needle 10.

As described above, the apparatus for loading a follicular unit into a needle for hair implant according to an embodiment of the present invention can provide a first instrument capable of accurately and quickly loading a follicular unit to the first needle for hair implant. Here, the first instrument includes the second needle having a slit to transmit a follicular unit, the first slitless needle used to implant the follicular unit to a human body, a push rod coupled to the second needle to push the follicular unit to the interior of the first needle to insert the follicular unit to the interior of the first needle, and a positioning jig serving to align the first needle and the second needle to be tightly attached. By the first instrument, a time for hair transplant procedure can be relatively reduced and a burden of a user such as surgeon or a patient may be reduced.

Also, the apparatus for loading a follicular unit into a needle for hair implant according to an embodiment of the present invention can provide the second instrument having any one of tweezers, stent, and an intake device in order to directly load a follicular unit to the first needle for hair implant. Here, the tweezer rod of the second instrument may be formed to be as thin as to be inserted into the first needle. The tweezers connected to the tweezer rod may directly grip and pull the follicular unit to easily load the follicular unit to the interior of the first needle.

Also, the apparatus for loading a follicular unit into a needle for hair implant according to an embodiment of the present invention can provide the first device in the form of a robot or a mechanism implementing an operational principle of the second instrument. Here, the first device has an advantage of easily loading a plurality of first needles to a cartridge for hair transplant equipment by a gripper.

Also, the apparatus for loading a follicular unit into a needle for hair implant according to an embodiment of the present invention can provide the second device in the form of a robot or a mechanism implementing an operational principle of the second instrument. Here, the second device has an advantage of quickly loading a plurality of first needles to a cartridge by a sweeper.

Also, the apparatus for loading a follicular unit into a needle for hair implant according to an embodiment of the present invention can provide a third device in the form of a robot or a mechanism implementing an operational principle of the first instrument. Here, the third device has an advantage of easily and quickly loading a plurality of first needles to the cartridge for hair implant by the push rod, the second needle, and the sweeper.

A number of exemplary embodiments have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for loading a follicular unit to a needle for hair implant, the apparatus comprising:
   a first needle, the first needle being a slitless needle having a hollow body and having one end and another end, the one end having a tubular shape and a blunt surface and the other end having a wedge shape viewed from a side view; and
   a first instrument configured to push the follicular unit to an interior of the first needle from a direction of the one end of the first needle to load the follicular unit into the interior of the first needle, the first instrument being hollow and including a slit on one side of the first instrument, the slit extending from one end of the first instrument along a length of the one side of the first instrument less than an entire length of the first instrument,
   wherein an inner diameter of the first instrument is configured to receive the follicular unit to insert the follicular unit into the first needle.

2. The apparatus of claim 1, wherein the first instrument further comprises:
   a second needle including the slit, the slit being on one side of the second needle, the slit extending from one end of the second needle along a length of the second needle less than an entire length of the second needle;
   a positioning jig having an insertion hole into which the first needle and the second needle are inserted, the insertion hole extending in a length direction of the positioning jig, the positioning jig coupled between the first needle and the second needle to position a center length axis of the second needle relative to a center length axis of the first needle,
   a push rod inserted into an interior of the second needle in order to push the follicular unit from the second needle toward an internal space of the first needle.

3. The apparatus of claim 2, wherein the positioning jig comprises:
   a front portion of the insertion hole having an inner diameter into which the one end of the first needle having the tubular shape is inserted; and a rear portion of the insertion hole having an inner diameter into which the one end of the second needle with the slit is inserted, the another end of the second needle having a flat shape viewed from a side view, wherein the front portion and the rear portion are integrally connected to each other and the inner diameter of the front portion and the inner diameter of the rear portion are equal.

4. The apparatus of claim 2, wherein the positioning jig comprises:
a front portion in which the follicular unit to be transmitted toward the first needle is disposed within the positioning jig, the front portion including a jig slit formed on one side of the positioning jig and extending from one end of the positioning jig along a length of the positioning jig less than an entire length of the positioning jig, and the front portion is configured to receive the one end of the first needle having the tubular shape; and
a rear portion integrally formed at the rear of the positioning jig and having a guide hole into which the push rod is inserted.

5. The apparatus of claim 2, wherein the positioning jig comprises:
a front portion of the insertion hole having an inner diameter into which the one end of the first needle having the tubular shape is inserted;
a rear portion of the insertion hole having an inner diameter into which the one end of the second needle having the slit is inserted; and
a middle portion of the insertion hole formed between the front portion and the rear portion, the middle portion having an inner diameter smaller than an inner diameter of the front portion and the inner diameter of the rear portion, and the middle portion having a stop protrusion configured to stop the second needle from passing through the positioning jig, the stop protrusion having a size such that the push rod is insertable to pass through the stop protrusion.

6. The apparatus of claim 5, wherein the positioning jig has a wedge portion formed at the rear end of the middle portion to receive a sharp end portion of the one end of the second needle, the wedge portion shaped so as to be press-fit to the sharp end portion of the second needle.

7. The apparatus of claim 2, wherein the push rod further comprises a groove configured to receive a hair member, and
wherein the groove extends along a length of the push rod less than an entire length of the push rod, and
wherein the groove extends to one end of the push rod inserted into the second needle.

8. The apparatus of claim 7, wherein the push rod comprises:
a spring support formed in a portion spaced apart from the groove; and
a spring coupled to the spring support and extending from the spring support toward the one end of the push rod, and
wherein one end of the spring is in contact with a side surface of the spring support and another end of the spring is in contact with an outer end surface of the second needle.

9. The apparatus of claim 8, wherein the one end of the spring is fixed by a first fixture of the spring support, and the another end of the spring is fixed by a second fixture of the outer end surface of the second needle.

10. An apparatus for loading a follicular unit into a needle for hair implant, the apparatus comprising:

a first needle, the first needle being a slitless needle, having a hollow body, and having one end and another end, the one end having a tubular shape and a blunt surface and the another end having a wedge shape viewed from a side view; and
an instrument configured to pull the follicular unit toward the first needle to load the follicular unit to an interior of the first needle, the instrument configured to extend through the first needle,
wherein the instrument has a first end that expands to have a first diameter upon exiting the first needle and contracts upon contacting the first needle in an insertion motion of the first end into the first needle to a second diameter less than the first diameter,
wherein the first end of the instrument is hollow and has an inner diameter such that when the first end of the instrument grips a hair member of the follicular unit upon contracting around the hair member, the combined diameters of the hair member and the first end of the instrument fit within an interior of the first needle,
wherein the first end of the instrument is open to a hollow interior of the first end of the instrument, such that the hollow interior of the first end of the instrument remains exposed when the instrument contracts, and
wherein the first end of the instrument is configured to expand upon being removed from the one end of the first needle, to thereby leave a hair bulb member of the follicular unit within the first needle while the hair member of the follicular unit extends outward from the one end of the first needle.

11. The apparatus of claim 10, wherein the instrument comprises:
tweezers formed of legs at the first end of the instrument to grip or release the hair member; and
a tweezer rod configured to have a diameter inserted into the interior of the first needle and connected to the tweezers,
wherein when the tweezer rod moves, outer surfaces of the tweezers come into contact with a hole edge of the first needle and the tweezers contract to grip the hair member.

12. The apparatus of claim 11, wherein the instrument further comprises a guide tube inserted into the first needle and interposed between the tweezer rod and the first needle.

13. The apparatus of claim 10, wherein the instrument further comprises:
a stent having a mesh structure for gripping or releasing the hair member the stent having a diameter such that a combined diameter of the stent and the hair member are movable within the first needle; and
a stent rod connected to the stent and having a diameter insertable into the interior of the first needle,
wherein when the stent rod moves, an outer surface of the stent comes into contact with the hole edge of the first needle and, as the stent contracts, the stent grips the hair member.

14. The apparatus of claim 13, wherein, as the stent rod moves forwards or backwards in a length direction within the first needle, or as the stent rod is rotated in a circumferential direction the stent connected to the stent rod and having elastic force expands or contracts.

15. An apparatus for loading a follicular unit into a needle for hair implant, the apparatus comprising:
a first needle, the first needle being a slitless needle having a hollow body and having one end and another end, the one end having a tubular shape and a blunt surface and the another end having a wedge shape viewed from a side view;

an intake tube inserted into an interior of the first needle to pull the follicular unit toward the first needle based on receiving intake pressure from an external pneumatic device, the intake pressure being lower than negative pressure formed by the external pneumatic device or atmospheric pressure; and a holder, comprising:
a needle mounting recess for receiving the first needle;
a follicular unit mounting recess at one end of the needle mounting recess, the follicular unit mounting recess having a width that increases as a distance from the needle mounting recess increases; and
a base including a through-hole,
wherein a length of the needle mounting recess corresponds to a length of the first needle when the first end of the first needle rests against the base, and
wherein the through-hole is aligned with an opening in the first end of the first needle when the first end of the first needle rests against the base, and the intake tube is inserted through the through-hole to be inserted into the interior of the first needle.

16. The apparatus of claim 15, wherein the holder has a plurality of the needle mounting recesses for disposing a plurality of the first needles, a plurality of the through holes along the base, and a plurality of the follicular unit mounting recesses provided on an opposite side of the plurality of needle mounting recesses from the plurality of through holes,
wherein the apparatus for loading the follicular unit includes a gripper device configured to grip the plurality of first needles in the holder and transfer the plurality of first needles to an interior of a cartridge,
wherein the intake tube includes a plurality of intake tubes,
wherein the follicular unit is tightly attached to an end of one of the plurality of intake tubes by the intake pressure, and
wherein removing the one of the plurality of intake tubes from the first needle stops the intake pressure from being generated in the one of the plurality of intake tubes to thereby allow the follicular unit to be loaded the interior of the first needle.

17. The apparatus of claim 15, wherein the holder includes a plurality of the needle mounting recesses, a plurality of the through holes arranged along the base, and a plurality of the follicular unit mounting recesses provided on an opposite side of the plurality of needle mounting recesses from the plurality of through holes;
a cartridge disposed on one side of the holder; and
a sweeper disposed on the other side of the holder and configured to sweep the plurality of first needles positioned on the plurality of needle mounting recesses into an interior of the cartridge.

18. The apparatus of claim 15, further comprising:
a base plate,
wherein the holder is installed on the base plate,
wherein the holder includes a plurality of the needle mounting recesses, and a plurality of the through holes aligned with centers of the plurality of needle mounting recesses on one side of the plurality of needle mounting recesses;
a cartridge mounting/dismounting block installed on the base plate, tightly attached to an outer surface of the holder in a length direction, the cartridge mounting/dismounting block configured to allow a cartridge to be inserted therein;
a sweeper slidably coupled to the holder and configured to sweep the plurality of first needles respectively positioned on the plurality of needle mounting recesses toward an interior of the cartridge;
a positioning jig installed on the base plate, tightly attached to a rear surface of the holder and configured to have a plurality of guide grooves provided in a direction in which the plurality of insertion holes of the holder extends;
a guide rail installed on the base plate and configured to extend backwards of the positioning jig;
a moving block coupled to the guide rail to move along the guide rail;
a first moving frame rotatably coupled to a hinge recess of the moving block and configured to move a second needle through an intake tube or a coupling hole of the holder; and
a second moving frame configured to move a push rod positioned within the second needle on the basis of the first moving frame in order to push the follicular unit from the second needle to load the follicular unit to an interior of the first needle.

19. The apparatus of claim 18, further comprising a spring interposed between a rear surface of a front portion of the first moving frame and a front surface of the second moving frame in order to transmit power.

\* \* \* \* \*